US006448377B1

(12) United States Patent
Kobilka et al.

(10) Patent No.: US 6,448,377 B1
(45) Date of Patent: Sep. 10, 2002

(54) MODIFIED G PROTEIN SUNBUNITS

(75) Inventors: Brian Kobilka; Tae Weon Lee, both of Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/672,239

(22) Filed: Sep. 27, 2000

(51) Int. Cl.$^7$ .................. C07K 17/00; G01N 33/58
(52) U.S. Cl. .................. 530/350; 435/7.1
(58) Field of Search ............. 530/350; 435/7.1

(56) References Cited

U.S. PATENT DOCUMENTS 6,280,934 B1 * 8/2001 Madden et al. ............. 435/6

FOREIGN PATENT DOCUMENTS

WO    WO-97/11159    * 3/1997

OTHER PUBLICATIONS

Seifert, R. et al., "Reconstitution of beta20adrenoreceptor–GTP–binding–protein interaction in Sf9 cells", Eur. J. Biochem., vol. 255, pp. 369–382 (1998).*

Remmers, A.E. et al., "Partial G Protein Activation by Fluorescent Guanine Nucleotide Analogs", J. Biol. Chem., vol. 271, pp. 4791–4797 (1996).*

Bertin B. et al., "Cellular signaling by an agonist–activated receptor/Gsalpha fusion protein", PNAS USA, vol. 91, pp. 8827–8831 (1994).*

Chidiac et al., "Agonist–Induced Modulation of Inverse Agonist Efficacy at the beta2–Adrenergic Receptor", Mol. Pharm. vol. 50, pp. 662–669 (1996).*

Seifert R. et al., "Examining the efficiency of receptor/G–protein coupling with a cleavable beta–2 adrenoreceptor–Gs alpha fusion protein", Eur. J. Biochem., vol. 260, pp. 661–666 (Mar. 1999).*

Bond, Richard (1997), "Do Recent Operational Studies Indicate that a Single State Model is No Longer Applicable to G Protein–Coupled Receptors." *Ann NY Acad Sci*, vol. 812:92–97.

Hopkinson et al. (2000), "Non–Competitive Antagonism of $\beta_2$–Agonist–Mediated Cyclic AMP Accumulation by ICI 118551 in BC3H1 Cells Endogenously Expressing Constitutively Active $\beta_2$–Adrenoceptors." *British Journal of Pharmacology*, vol. 131:124–130.

Mombaerts, Peter (Oct. 22, 1999), "Seven–Transmembrane Proteins as Odorant and Chemosensory Receptors." *Science*, vol. 286:707–711.

Strange, Phillip G. (1999), "Agonism and Inverse Agonism at Dopamine $D_2$–Like Receptors." *Clinical and Experimental Pharmacology and Physiology*, vol. 2(Suppl):S3–S9.

* cited by examiner

*Primary Examiner*—Kenneth R. Horlick
*Assistant Examiner*—Teresa Strzelecka
(74) *Attorney, Agent, or Firm*—Bozicevic, Field & Francis LLP; Carol L. Francis; David D. Phinney

(57) ABSTRACT

The present invention provides modified G protein α-subunits which are characterized by constitutive localization to the plasma membrane; enhanced binding to one or more of the normal receptor binding partners for that α-subunit; and efficient binding to and activation of G protein binding partners. The distribution of these modified α-subunits, which are "tethered" to the plasma membrane, allows the regulation of receptor-G protein coupling, and thus G-protein signaling, in various biological systems.

31 Claims, 23 Drawing Sheets

SEQUENCE LISTING

<160> NUMBER OF SEQ ID NOS: 9

<210> SEQ ID NO 1
<211> LENGTH: 8
<212> TYPE: PRT
<213> ORGANISM: Homo sapiens

<400> SEQUENCE: 1

Asp Tyr Lys Asp Asp Asp Asp Lys
1               5

<210> SEQ ID NO 2
<211> LENGTH: 8
<212> TYPE: PRT
<213> ORGANISM: Homo sapiens

<400> SEQUENCE: 2

Asp Tyr Lys Asp Glu Asp Asp Lys
1               5

```
<210> SEQ ID NO 3
<211> LENGTH: 9
<212> TYPE: PRT
<213> ORGANISM: Homo sapiens

<400> SEQUENCE: 3

Ala Trp Arg His Pro Gln Phe Gly Gly
 1               5

<210> SEQ ID NO 4
<211> LENGTH: 13
<212> TYPE: PRT
<213> ORGANISM: Homo sapiens

<400> SEQUENCE: 4

Tyr Pro Tyr Asp Val Pro Asp Tyr Ala Ile Glu Gly Arg
 1               5                  10

<210> SEQ ID NO 5
<211> LENGTH: 7
<212> TYPE: PRT
<213> ORGANISM: Homo sapiens

<400> SEQUENCE: 5

Thr Val Thr Asn Tyr Phe Arg
 1               5

<210> SEQ ID NO 6
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 6
gccgactaca aggacgatga tgac                                              24

<210> SEQ ID NO 7
<211> LENGTH: 33
<212> TYPE: DNA
<213> ORGANISM: Artificial Sequence
<220> FEATURE:
<223> OTHER INFORMATION: synthesized oligonucleotide

<400> SEQUENCE: 7
actagtctcg agaaagtctt ccgtgcctgg gag                                    33

<210> SEQ ID NO 8
<211> LENGTH: 33
<212> TYPE: DNA
<213> ORGANISM: Artificial Sequence
<220> FEATURE:
<223> OTHER INFORMATION: synthesized oligonucleotide

<400> SEQUENCE: 8
ctcgagacta gtgtgggcca tcaaggtact gtg                                    33

<210> SEQ ID NO 9
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 9
```

-continued

```
gtcgatcagc tggtactcgt t                                              21

<210> SEQ ID NO 10
<211> LENGTH: 27
<212> TYPE: DNA
<213> ORGANISM: Artificial Sequence
<220> FEATURE:
<223> OTHER INFORMATION: Tobacco Etch Virus protease cleavage site

<400> SEQUENCE: 10
actagtgaaa atctttattt ccaggga                                        27
```

US 6,448,377 B1

MODIFIED G PROTEIN SUNBUNITS

GOVERNMENT RIGHTS

The United States Government may have certain rights in this application pursuant to National Institutes of Health Grant 2ROINS28471.

FIELD OF THE INVENTION

The present invention relates to molecules involved in cell signaling, and in particular with molecules involved in transducing a signal through a G protein coupled receptor.

BACKGROUND OF THE INVENTION

The actions of many extracellular signals are mediated by the interaction of guanine nucleotide-binding regulatory proteins (G proteins) and G-protein coupled receptors (GPCRs). Individual GPCRs activate particular signal transduction pathways through binding to G proteins, which in turn transduce a signal to the cell to elicit a response from the cell. GPCRs are known to respond to numerous extracellular signals, including neurotransmitters, drugs, hormones, odorants and light. The family of GPCRs has been estimated to include several thousands members, fully more than 1.5% of all the proteins encoded in the human genome. The GPCR family members play roles in regulation of biological phenomena involving virtually every cell in the body. The sequencing of the human genome has led to identification of numerous GPCRs; although the ligands and functions of many of these GPCRs are known, a significant portion of these identified receptors are without known ligands. These latter GPCRs, known as "orphan receptors", also generally have unknown physiological roles.

Many available therapeutic drugs in use today target GPCRs, as they mediate vital physiological responses, including vasodilation, heart rate, bronchodilation, endocrine secretion, and gut peristalsis. See, eg., Lefkowitz et al., Ann. Rev. Biochem. 52:159 (1983); Gilman, A. G. (1987) Annu. Rev. Biochem 56: 615–649; Hamm, H. E. (1998) *JBC* 273: 669–672; Ji ,T. H. (1998) *JBC* 273: 17229–17302. Kanakin, T. (1996) *Pharmacological review,* 48:413–463; Gudermann T. and Schultz, G. (1997), *Annu. Rev. Neurosci.,* 20: 399–427. In fact, it has been estimated that more than 50% of the drugs in use clinically in humans at the present time are directed at GPCRs, including the adrenergic receptors (ARs). For example ligands to beta ARs are used in the treatment of anaphylaxis, shock, hypertension, hypotension, asthma and other conditions.

Although in general GPCRs require agonist binding for activation, agonist-independent signaling activity has been well documented in the native form of a variety of GPCRs. This spontaneous activation of GPCRs occurs, in both normal and pathological processes, where a GPCR cellular response is generated in the absence of a ligand. For example, native dopamine D1B and prostaglandin EP1b receptors have been found to possess constitutive activity (Tiberi and Caron 1994; Hasegawa et al. 1996). In addition, a number of GPCRs, for example, receptors for thyroid-stimulating hormone (Vassart et al. 1995), have mutants that exhibit agonist-independent activity and cause disease in humans. Experimentally, several single amino acid mutations have produced agonist independent activity in GPCRs. $\beta 2$ and $\alpha 2$ adrenergic receptors, for example, mutated at single sites in the third cytoplasmic loop show constitutive activity (Ren et al. 1993; Samama et al. 1994). In another example, a truncation deletion of the carboxyl terminus in the thyrotropin releasing hormone receptor renders the receptor constitutively active (Nussenzveig et al. 1993; Matus-Leibovitch et al. 1995) and a smaller deletion in the second extracellular loop of the thrombin receptor causes constitutive activity (Nanevicz et al. 1995).

Increased spontaneous activity and/or basal activity of GPCRs can be decreased by inverse agonism of the GPCRs. Such methods are therapeutically important where diseases cause an increase in spontaneous GPCR activity, or where it is desirable to decrease the basal activity of GPCR. Thus, a technology for identifying inverse agonists of native and mutated GPCRs has important pharmaceutical applications. Furthermore, because certain constitutively active GPCRs can be tumorigenic, the identification of inverse agonists for these GPCRs can lead to the development of anti-tumor and/or anti-cell proliferation drugs. These compounds have become increasingly important, especially for the treatment of psychological disorders such as depression and bipolar disorder. Unfortunately, conventional assays are not particularly suited to reliably identify inverse agonists, as the activity of the GPCRs in response to an inverse agonist cannot be directly measured.

Since GPCRs and G protein signaling pathways are critical targets for therapeutics, there is a need in the art for fast, effective and reproducible methods for identifying agonists, antagonists and inverse agonists that modulate G protein signaling, and in particular compounds that regulate this signaling through a GPCR. The present invention addresses this need.

SUMMARY OF THE INVENTION

The present invention provides modified G protein $\alpha$-subunits which are characterized by 1) constitutive localization to the plasma membrane; 2) enhanced binding to one or more of the normal receptor binding partners for that $\alpha$-subunit; and 3) efficient binding to and activation of G protein binding partners. The distribution of these modified $\alpha$-subunits, which are tethered to the plasma membrane, allows the regulation of receptor-G protein coupling, and thus G-protein signaling, in various biological systems. Also encompassed in the present invention are nucleic acids encoding such modified G protein $\alpha$-subunits, and expression vectors containing such nucleic acids.

In particular, these modified G protein $\alpha$-subunits allow for enhanced activation of downstream signaling partners of G proteins, and thus can provide for assays having increased specificity. Thus, in one embodiment, the invention provides assays for identifying agonists, antagonists, and/or inverse agonists using a system comprising the modified G protein $\alpha$-subunits of the invention. The tethered $\alpha$-subunits provided in the assay improve the response of the GPCR to its ligand, and thus these assays are useful in identifying agonists, antagonists, and/or inverse agonists that activate a GPCR. The assays comprise contacting a membrane or cell comprising tethered $\alpha$-subunits with a ligand and determining the activation of the GPCR via stimulation of a downstream binding partner. The downstream binding partner used in the assay will depend upon the transduction pathway for a particular class of G protein. For example, if a tethered $G_s\alpha$ is used in the assay, the assay may measure levels of AC stimulation. Such assays can be whole cell assays, and preferably are membrane assays.

In another embodiment, the invention provides methods for identifying the presence of a chemical that acts as a ligand for a GPCR via an assay that directly measures G protein signaling through measurement of activation of a G protein binding partner. The ligands can be identified in an assay whereby a sample suspected of containing the chemical is contacted with either whole cells or membranes comprising tethered G protein α-subunits. The presence of the ligands can be identified by measuring G protein activation of a signaling partner, e.g., AC. For example, the assay can be used to identify the presence of a drug such as an opioid in a sample, as the opioid binds to and activates the opioid receptor, which is a GPCR.

In yet another embodiment, the invention provides methods for determining the ligand for an orphan GPCR via an assay that directly measures G protein signaling through measurement of activation of downstream binding partner. The ligands can be identified using an assay with either whole cells or membranes comprising tethered G protein α-subunits. The ligands can be identified by measuring G protein activation of a signaling partner, e.g., AC.

In yet another embodiment, the invention provides assays for identifying the G proteins involved in the signaling of a specific GPCR using an assay comprising membranes with different tethered G protein α-subunits. By assaying the activity in membranes coexpressing the GPCR and different tethered α-subunits, and measuring the activation of the G protein involved in specific G protein signaling responses, the specific G protein involved in specific GPCR signaling events can be determined.

One object of the present invention is to develop rapid and sensitive bioassays for evaluating new agonists, antagonists and/or inverse agonists for GPCRs.

Another object of the present invention is to develop a strategy for identifying ligands for GPCRs.

Yet another object of the present invention is to develop a strategy for identifying GPCRs involved in different biological processes, including disease.

Yet another object of the invention is to identify the presence of a particular ligand in a sample, e.g., the presence of a drug such as an opioid.

An advantage of the invention is that the assays can be performed using membranes, which increases both the ease of performing the assay and the efficacy of the assay.

Another advantage is that assays of the invention allow high throughput screening of GPCR activity.

Yet another advantage of the invention is that the assays of the invention directly measure GPCR activity, and thus are less labor-intensive than conventional methods for determining GPCR activity.

Yet another advantage of the invention is that the modified G protein α-subunits can be epitope tagged. This provides a direct method for detecting these proteins, as well as providing methods for affinity purification.

Yet another advantage is that the modified G protein α-subunits can be designed to have a protease site between the active portion of the subunit and the membrane tether. This allows for isolation of the subunit based on the membrane tether, and subsequent removal of the membrane tether.

These and other objects, advantages, and features of the invention will become apparent to those persons skilled in the art upon reading the details of the proteins and assays as more fully described below.

BRIEF DESCRIPTION OF THE DRAWINGS

(FIG. 8).

DETAILED DESCRIPTION OF PREFERRED EMBODIMENTS

Figure 1:
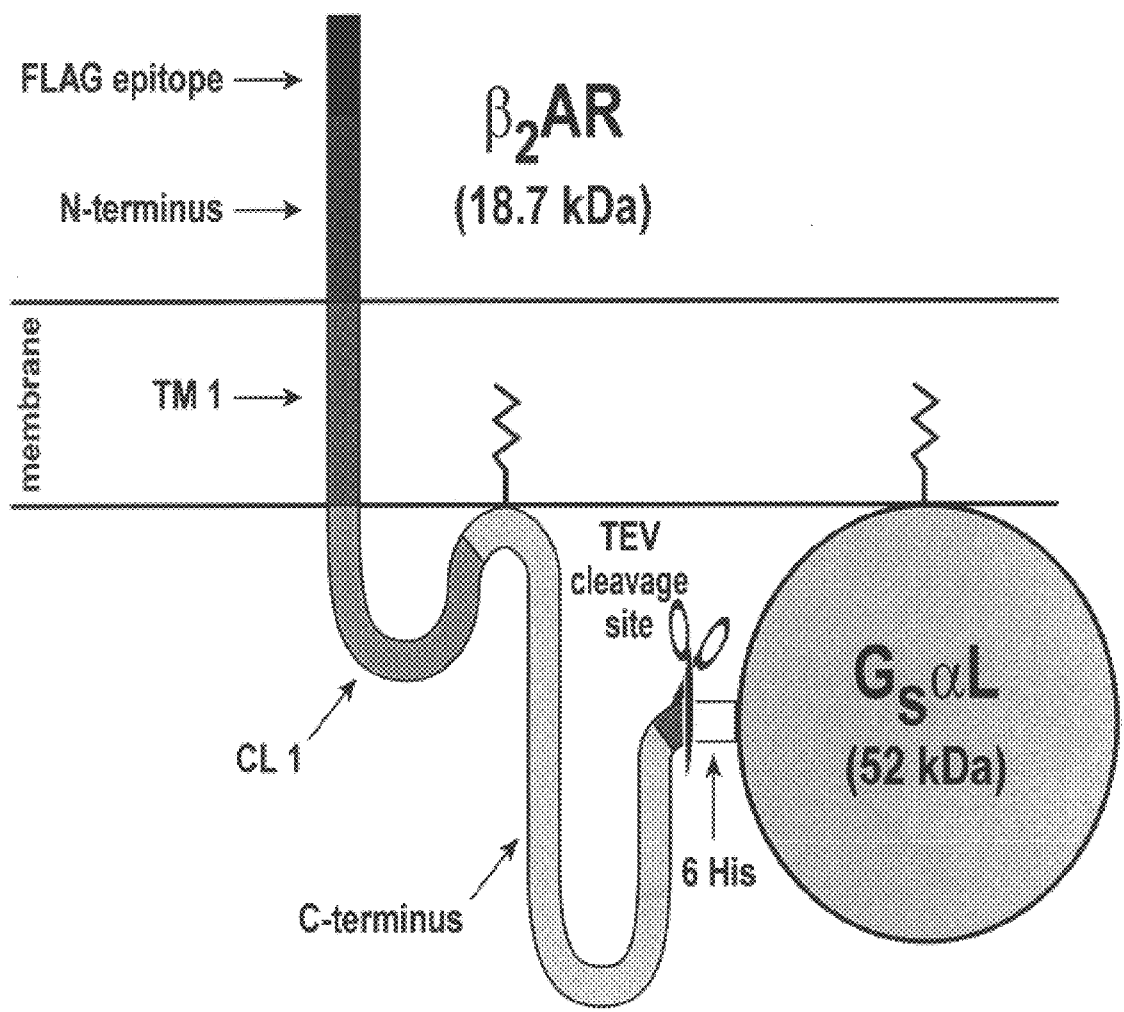
FIG. 1 is a schematic structure of membrane-tethered $G_s\alpha$.

Before the present modified proteins and methods are described, it is to be understood that this invention is not limited to particular constructs and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a subunit" includes a plurality of such subunits and reference to "the ligand" includes reference to one or more ligands and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "agonist" as used herein refers to a molecule or substance that binds to or otherwise interacts with a receptor or enzyme to increase activity of that receptor or enzyme.

The term "antagonist" as used herein refers to a molecule that binds to or otherwise interacts with a receptor or enzyme to inhibit the activation of that receptor or enzyme.

The term "inverse agonist" as used herein refers to a molecule that binds to or otherwise interacts with a receptor to inhibit the basal activation of that receptor or enzyme.

The term "ligand" as used herein refers to a naturally occurring or synthetic compound that binds to a protein receptor. Upon binding to a receptor, ligands generally lead to the modulation of activity of the receptor. The term is intended to encompass naturally occurring compounds, synthetic compounds and/or recombinantly produced compounds. As used herein, this term can encompass agonists, antagonists, and inverse agonists.

The term "receptor" as used herein refers to a protein normally found on the surface of a cell which, when activated, leads to a signaling cascade in a cell.

The term "functional interaction" as used herein refers to an interaction between a receptor and ligand that results in modulation of a cellular response. These may include changes in membrane potential, secretion, action potential generation, activation of enzymatic pathways and long term structural changes in cellular architecture or function.

The term "constitutive localization" as used herein refers to the localization of a modified α, subunit that, unlike wild-type α subunits, remains localized at the plasma membrane following activation of the G protein complex. In a cell expressing a modified Gα subunit of the invention, "constitutive localization" refers to preferably at least 75% of the modified Gα subunits being retained at the membrane following G protein activation, more preferably at least 85% of the modified Gα subunits being retained at the membrane following G protein activation, and even more preferably at least 95% of the modified Gα subunits being retained at the membrane following G protein activation. Constitutive localization can be accomplished by, for example, tethering of the subunit to the cell membrane.

The terms "tethered", "tethering" and the like as used herein refer to a physical modification of a protein (e.g., the addition of a domain or fatty acylation site) that causes the protein to be localized to the plasma membrane. For example, a tethered Gα a of a preferred embodiment of the invention comprises a transmembrane spanning domain that anchors the protein into the plasma membrane, thus preventing release of the Gα into the cytosol.

The term "G protein subunit" as used herein can refer to any of the three subunits, α, β, or γ, that form the heterotrimeric G protein. The term also refers to a subunit of any class of G protein, e.g., $G_s$, $G_i/G_o$, $G_q$ and $G_z$. In addition, recitation of a specific subunit (e.g., Gα) is intended to encompass that subunit in each of the different classes, unless the class of G protein is specifically otherwise specified.

The terms "G protein coupled receptors" and "GPCRs" as used interchangeably herein include all subtypes of the opioid, muscarinic, dopamine, adrenergic, adenosine, rhodopsin, angiotensin, serotonin, thyrotropin, gonadotropin, substance-K, substance-P and substance-R receptors, melanocortin, metabotropic glutamate, or any other GPCR known to couple via G proteins. This term also includes orphan receptors which are known to couple to G proteins, but for which no specific ligand is known.

The terms "epitope tagged protein" and "epitope tagged Gα" and the like are used interchangeably herein to mean an artificially constructed protein having one or more heterologous epitope domain(s).

The term "biological system" as used herein refers to any system in which the molecular responses to the activation of G proteins, e.g., activation through GPCRs, can be measured. The biological systems may be in vitro (e.g., membrane preparations or cell culture).

The term "efficient binding" as used herein in reference to a modified subunit refers to binding that is comparable to the binding capacity of the corresponding wild-type subunit. Preferably, efficient binding refers to binding that is at least 60% that of the wild-type subunit, more preferably it refers to binding that is at least 75% that of the wild-type subunit, more preferably it refers to binding that is at least 90% that of the wild-type subunit.

The term "downstream effector of G protein signaling" as used herein refers to any molecule that is involved in the transduction of a signal from a G protein. This includes molecules that directly bind to a G protein subunit as well as to molecules indirectly involved in the signaling that are indicative of the level of activation of the G protein (e.g., GDP levels).

The abbreviations used herein include:
GPCR for G protein-coupled receptor;
β2 AR for β2 adrenoceptor;
Gα, for an α subunit of a G-protein $G_s\alpha$, for an $\alpha$ subunit of the stimulatory G-protein;
tetG$\alpha$, for a membrane-tethered G$\alpha$;
tetG$_s\alpha$, for a membrane-tethered G$_s\alpha$;
AC for adenylyl cyclase;
[$^3$H]DHA for [$^3$H]dihydroalprenol;
GTP$\gamma$S for guanosine 5'-O-(3-thiotriphosphate);
ISO for (−)isoproterenol;
ALP for (−) alprenolol; and
ICI for ICI-118,551.

GENERAL ASPECTS OF THE INVENTION

The present invention is based on the finding that redistribution of G-protein $\alpha$-subunits can be achieved by tethering these molecules to the plasma membrane. Compared to wild-type G-protein $\alpha$-subunits, the tethered $\alpha$-subunits (tetG$\alpha$) coupled more efficiently to their partner receptors, e.g., tetG$_s\alpha$ bound more efficiently to the $\beta$2 AR and the D1 dopamine receptor than did wild-type G$_s\alpha$. In addition, this increased receptor binding did not interfere with G protein interaction with other molecules involved in G protein signaling, e.g., the membrane tether of G$_s\alpha$ did not prevent the coupling of tetG$_s\alpha$ to AC.

For example, G$_s\alpha$ has been shown to dissociate from the plasma membrane following activation of the G protein complex in several cell lines (See, e.g., Iiri, T. et al., (1996) *Proc. Natl. Acad. Sci. U.S.A.* 93:14592–7). The effect of tethering G$_s\alpha$ to the plasma membrane, e.g., by using the first membrane-spanning domain of the $\beta$2 adrenoceptor as a membrane anchor, led to the surprising finding that tetG$_s\alpha$ coupled much more efficiently to the $\beta$2 adrenoceptor than did the wild-type G$_s\alpha$, even when the density of wild-type G$_s\alpha$ was at least 10-fold higher than the density of tetG$_s\alpha$.

In addition, restricting the mobility of G$\alpha$ facilitates receptor-mediated rebinding of GTP$\gamma$S to tetG$\alpha$ molecules that have lost GTP$\gamma$S. Thus, by restricting the mobility of G$\alpha$ relative to the membrane, it is possible to increase the apparent binding capacity of a G protein for GTP$\gamma$S. The high efficiency of coupling between tetG$_s\alpha$ and the $\beta$2 adrenoceptor results from restricting the mobility of G$_s\alpha$, which promotes physical interactions with the receptor by providing increased access of the G$_s\alpha$ to the receptor.

The most striking functional differences between tetG$\alpha$ and wild-type G$\alpha$ were observed with respect to receptor-stimulated GTPase activity and GTP$\gamma$S binding. The steady-state GTPase activity measures the ability of receptor to stimulate multiple G protein activation/inactivation cycles. Without being bound to a theory, these GTPase results can be explained by tetG$_s\alpha$ being capable of repeated cycles of interaction with an agonist-liganded receptor while the wild-type G$_s\alpha$ was only capable of a single interaction because after activation G$\alpha$ dissociated from the receptor. GTPase activity is therefore limited by the rate of diffusion of new G$\alpha$ molecules to receptor molecules.

Mammalian G Proteins and G Protein $\alpha$-subunits of the Invention

The known mammalian G-proteins are divided into four subtypes: G$_s$, G$_i$/G$_o$, G$_q$ and G$_z$. This typing is based on the effect of activated G-proteins on enzymes that generate second messengers and on their sensitivity to cholera and pertussis toxin. The division of mammalian G proteins also appears to be evolutionarily ancient since there are comparable subtypes in invertebrate animals. Members of two subtypes of G-proteins control the activity of adenylyl cyclases (ACs). Activated G$_s$ proteins increase the activity of ACs, whereas activated G$_i$ proteins (but not G$_o$) inhibit these enzymes. G$_s$ proteins are also uniquely activated by cholera toxin.

The G$\alpha$ subunits have binding sites for a guanine nucleotide and intrinsic GTPase activity. This structure and associated mechanism are shared with the monomeric GTP-binding proteins of the ras superfamily. Prior to activation the complex contains bound GDP:G$\alpha$GDP$\beta\gamma$, activation involves the catalyzed release of GDP followed by binding of GTP and concurrent dissociation of the complex into two signaling complexes: G$\alpha$GTP and $\beta\gamma$. Signaling through G$\alpha$GTP, the more thoroughly characterized pathway, is terminated by GTP hydrolysis to GDP. G$\alpha$GDP then reassociates with $\beta\gamma$ to reform the inactive, heterotrimeric complex.

The modified G$\alpha$ subunits of the invention are characterized by localization at the membrane and by functional interactions with its binding partners, including GPCRs, GTP, downstream effector molecules, and $\beta\gamma$ subunits. In addition, these modified G$\alpha$ subunits have a limited lateral mobility within the plasma membrane. The modified G$\alpha$ subunits of the present invention cannot be stripped from the plasma membrane with concentrations of salt or with urea, in a concentration that will release wild-type G$\alpha$ subunits. For example, 6M urea is generally used to strip wild-type G protein subunits from the membrane. See, e.g., Hellmich, M. R. et al., (1997) PNAS; Soren P. S. et al., (1999) JBC. 274:17033–17041. The modified G$\alpha$ subunits of the invention generally remain constitutively localized to the plasma membrane under conditions such as 6M urea.

The modified G$\alpha$ subunits of the invention can be produced by adding any functional domain, motif, or moiety that will allow association of the G$\alpha$ subunit with both the receptor and its other binding partners (including $\beta\gamma$), but which retains the G$\alpha$ at the plasma membrane following G protein activation. Preferably, the tethered G$\alpha$ subunits are produced by introducing at least one transmembrane domain to the G$\alpha$ protein. The transmembrane domain is preferably positioned at the N-terminus of the protein, although it can be placed in any region provided it does not interfere with receptor activation or binding and/or activation of downstream proteins. In an exemplary embodiment, a transmembrane domain from the $\beta$2 AR is fused to the n-terminus of a G$\alpha$ subunit to produce the tethered G$\alpha$ subunit (FIG. 1).

In addition, G protein $\alpha$-subunits have a variety of post-translational lipid modifications. G$_i\alpha$, G$_o\alpha$, and G$_z\alpha$ are myristoylated by amide linkage at their N-terminal glycine residues (Buss, J. et al., (1987)*Proc. Natl. Acad. Sci. U.S.A.* 84:7493–7; Mumby, S. et al., (1990) *Proc. Natl. Acad. Sci. U.S.A.* 87, 728–32), and they are also palmitoylated at distinct sites. G$_s\alpha$ and G$_q\alpha$ are palmitoylated by a thioester bond at N-terminal cysteine residues (Wedegaertner, P. B. et al., (1993) *J. Biol. Chem.* 268, 25001–8; Mumby, S. M et al., (1994) *Proc.Natl. Acad. Sci. U.S.A.* 91, 2800–4). Modifications of these preexisting sites can be used to allow constitutive localization of tetG$\alpha$ to the plasma membrane. Alternatively, new lipid modifications (e.g., addition of a fatty acylation site such as a farnesylation or gerangeranylation site) can be added to adhere the G$\alpha$ subunits more closely to the plasma membrane and to prevent release of the G$\alpha$ subunit upon stimulation.

Epitope Tagged tetG$\alpha$ Proteins

The invention also provides epitope-tagged tetG$\alpha$ proteins and nucleic acids encoding such proteins. These proteins comprise both the membrane tethering moiety and a heterologous epitope domain. By "heterologous" is meant that the two elements are derived from two different sources, e.g., the resulting chimeric protein is not found in nature. A variety of epitopes may be used to tag a protein, so long as the epitope (1) is heterologous to the naturally-occurring G$\alpha$ subunit, and (2) the epitope-tagged Gα subunit retains at least part and preferably all of the biological activity of the tetGα protein. Such epitopes may be naturally-occurring amino acid sequences found in nature, artificially constructed sequences, or modified natural sequences.

Recently, a variety of artificial epitope sequences have been described that have been shown to be useful for tagging and detecting recombinant proteins. One such tag, the eight amino acid FLAG marker peptide (Asp-Tyr-Lys-Asp-Asp-Asp-Asp-Lys) (SEQ ID NO:1), has a number of features which make it particularly useful for not only detection but also affinity purification of recombinant proteins (Brewer (1991) Bioprocess Technol. 2:239–266; Kunz (1992) J. Biol. Chem. 267:9101–9106). Inclusion of the FLAG epitope in recombinant proteins avoids the necessity for the development of a specialized scheme or functional assay for protein purification and circumvents need to raise antibodies against the tagged protein, the first four amino acids of this sequence comprising the antigenic site for -FLAG M1 and M2 monoclonal antibodies. The small octapeptide has a high degree of hydrophilicity, thus maximizing accessibility to -FLAG M1 and M2 monoclonal antibodies. A particularly useful feature is the calcium dependent binding of the -FLAG M1 monoclonal antibody to recombinant proteins containing the FLAG peptide. Removal of the $Ca^{2+}$ by chelation with EDTA allows for efficient immunoaffinity purification without denaturation.

A further advantage of the FLAG system is that it allows cleavage of the FLAG peptide from purified protein since the tag contains the rare five amino acid recognition sequence for enterokinase. The anti-FLAG M1 antibody requires an N-terminal FLAG sequence. A second anti-FLAG monoclonal antibody (anti-FLAG M2) has been employed in immunoaffinity purification of N-terminal Met-FLAG and C-terminal FLAG fusion proteins (Brizzard et al. (1994) Biotechniques 16:730–735). This antibody has, however, been found to cross-react with a splicing isoform of $Mg^{2+}$ dependent protein phosphatase beta (MPP beta) which contains a sequence motif with five out of eight amino acid residues identical to the FLAG peptide (Schafer (1995) Biochem. Biophys. Res. Commun. 207:708–714). Binding of an anti-FLAG M2 monoclonal antibody to the FLAG epitope is not calcium-dependent, but bound fusion proteins can be eluted by competition with FLAG peptide.

Additional artificial epitope tags include an improved FLAG tag having the sequence Asp-Tyr-Lys-Asp-Glu-Asp-Asp-Lys (SEQ ID NO:2), a nine amino acid peptide sequence Ala-Trp-Arg-His-Pro-Gln-Phe-Gly-Gly (SEQ ID NO:3) referred to as the "Strep tag" (Schmidt (1994) J. Chromatography 676:337–345), poly-histidine sequences, e.g., a poly-His of six residues which is sufficient for binding to IMAC beads, an eleven amino acid sequence from human c-myc recognized by monoclonal antibody 9E10, or an epitope represented by the sequence Tyr-Pro-Tyr-Asp-Val-Pro-Asp-Tyr-Ala-Ile-Glu-Gly-Arg (SEQ ID NO:4) derived from an influenza virus hemagglutinin (HA) subtype, recognized by the monoclonal antibody 12CA5. Also, the Glu-Glu-Phe sequence recognized by the anti- tubulin monoclonal antibody YL 1/2 has been used as an affinity tag for purification of recombinant proteins (Stammers et al. (1991) FEBS Lett. 283:298–302).

tetGα Proteins with Protease Sites

The present invention also provides modified Gα subunits having a protease cleavage site introduced into the protein, and preferably introduced between the portion of the protein responsible for the constitutive localization (e.g., the membrane tether) and the functional portion of the protein. This site can allow for purification of the modified subunit based on the site, e.g., purification using antibodies that recognize the protease epitope. In addition, the cleavage site allows the removal of the region responsible for purification following the purification of the protein. Exemplary cleavage sites that can be introduced into the modified Gα subunits of the invention include, but are not limited to, trypsin, chymotrypsin, pepsin, elastase, pronase, endoproteases (e.g., Arg-C, Asp-C, Glu-C, and Lys-C), endopeptidases such as Hepatitis C virus NS3 endopeptidase and tobacco etch virus proteases.

Assays of the Present Invention

Methods for detecting or identifying G protein activation through GPCRs are important for numerous applications in medicine and biology. The present invention provides methods including: (1) methods for rapidly and reproducibly screening for new drugs affecting selected GPCRs, (2) methods for identifying the native ligand for orphan GPCRs, (3) methods for detecting the presence of known chemicals that associate with GPCRs in a sample, e.g., drugs that activate GPCRs; and (4) methods for investigating molecules in signaling pathways involving G proteins. The basic assays described herein and variations thereof can also be used in other applications, as will be apparent to those skilled in the art upon reading the present application.

A significant advantage of the assays of the invention is that they can directly detect G protein activation through GPCRs either qualitatively or quantitatively, and thus are particularly amenable to high throughput screening of large numbers of GPCRs. This can be useful, for example, in determining the receptors activated by a particular drug or receptors that are activated upon exposure to a particular stimulus, such as an odor or taste (e.g., activation of olfactory GPCRs).

Biological Systems for Use in Assays of the Invention

Biological Systems for use in the present invention can be any system in which the molecular responses to the activation of GPCRs and/or G proteins can be monitored. This includes, but is not limited to, cells expressing GPCRs and modified Gα subunits and membranes comprising GPCRs and modified Gα subunits. Biological systems comprising cells can have endogenous GPCR expression and the introduction of a recombinant modified Gα subunits, e.g., via introduction of an expression vector containing sequences encoding the modified Gα subunit. Alternatively, the cells may have both a recombinant GPCR and a recombinant modified Gα subunit introduced via an expression vector. Membrane systems, for example, can be derived from either of these cell types. The membrane systems are preferred, as they provide enhanced sensitivity relative to whole cell systems.

GPCR polypeptides, each of which encompasses biologically active or immunogenic fragments or oligopeptides thereof, can be used for screening compounds that affect GPCR receptor activity by, for example, specifically binding the GPCR and affecting its function, thereby affecting GPCR activity and G protein activation.

Identification of such compounds can be accomplished using any of a variety of drug screening techniques. Of particular interest is the identification of agents that have activity in affecting GPCR function. Such agents are candidates for development of treatments for, conditions associated at least in part with GPCR activity. Of particular interest are screening assays for agents that have a low toxicity for human cells. The polypeptide employed in such a test can be free in solution, affixed to a solid support, present on a cell surface, or located intracellularly. The screening assays of the invention are generally based upon the ability of the agent to bind to a GPCR polypeptide, and/or elicit or inhibit a GPCR-associated biological activity through G protein activation and signaling (i.e., a functional assay or an assay using radioligand binding assays).

The term "agent" as used herein describes any molecule, e.g. protein or pharmaceutical, with the capability of altering (i.e., eliciting or inhibiting) or mimicking a desired physiological function of a GPCR. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts (including extracts from human tissue to identify endogenous factors affecting GPCRs) are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Preferably, the drug screening technique used provides for high throughput screening of compounds having suitable binding affinity to the GPCR, and/or eliciting a desired GPCR-associated response. For example, large numbers of different small peptide test compounds can be synthesized on a solid substrate, such as plastic pins or some other surface (see, e.g., Geysen WO Application 84/03564, published on Sep. 13, 1984), the peptide test compounds contacted with GPCR polypeptides, unreacted materials washed away, and bound GPCR detected by virtue of a detectable label or detection of a biological activity associated with GPCR receptor activity. The identified agents can then be tested for their ability to modulate the activity of a GPCR via an assay using a biological system comprising a GPCR and modified Gα subunits.

The invention also contemplates the use of competitive drug screening assays in which GPCR receptor-specific neutralizing antibodies compete with a test compound for binding of the GPCR polypeptide. In this manner, the antibodies can be used to detect the presence of any polypeptide that shares one or more antigenic determinants with a GPCR polypeptide.

Screening of Candidate Agents

A wide variety of assays may be used for identification of GPCR binding agents, including labeled in vitro binding assays, immunoassays for protein binding, and the like. For example, by providing for the production of large amounts of GPCR polypeptides, one can identify ligands or substrates that bind to, modulate or mimic the action of the proteins. The purified protein may also be used for determination of three-dimensional crystal structure, which can be used for modeling intermolecular interactions.

The screening assay can be a binding assay (e.g., to detect binding of a GTP analog to a modified Gα subunits), wherein one or more of the molecules may be joined to a label, and the label directly or indirectly provide a detectable signal. Various labels include radioisotopes, fluorescers, fluorescent GTP analogs (e.g., N-methyl-3'-O-anthranoyl (MANT) guanine nucleotide analogs, see Remmers A E and Neubig R R., *J Biol. Chem.* (1996) 271:4791–7), chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Identification and Design of Therapeutic Compounds

A major asset of the invention is its ability to vastly increase, over current methods, the rate at which compounds can be evaluated for their ability to act as agonists, antagonists, and/or inverse agonists for GPCRs. As additional GPCR genes are identified and characterized, the activity of these receptors in response to various compounds, as well as to methods such as site directed mutagenesis, can be used to gain detailed knowledge about the basic mechanisms at work in these receptors. A fundamental knowledge of the basic mechanisms at work in these receptors will be of great use in understanding how to develop promising new drugs and/or to identify the fundamental mechanisms behind specific tastes, smells and the like.

Assays using the modified Gα. can identify promising agonists and/or antagonists for specific receptors. In an exemplary assay, membranes or whole cells coexpressing tetGα and a target GPCR can be contacted with a candidate therapeutic, and the activity of the G protein activation through the receptor measured, e.g., by measuring GTPase activity, binding of GTP analogs, and/or activation of effector molecules such as AC. Agonists can be identified by their ability to increase GPCR activity over basal levels in the system. Antagonists can be identified by contacting the membranes or whole cells of the assay system with a native ligand or agonist and a candidate antagonist; compounds that inhibit the ability of the ligand or agonist to increase activity of the GPCR are identified as antagonists.

For example, GPCR-binding compounds can be screened for agonistic or antagonist action in a functional assay that monitors a biological activity associated with GPCR function such as effects upon intracellular levels of cations (e.g., calcium) in a host cell, calcium-induced reporter gene expression (see, e.g., Ginty 1997 Neuron 18:183–186), or other readily assayable biological activity associated with GPCR activity. Preferably, such a functional assay is based upon detection of a biological activity of the GPCR that can be assayed using high-throughput screening of multiple samples simultaneously, e.g., a functional assay based upon detection of a change in fluorescence which in turn is associated with a change in GPCR activity. Such functional assays can be used to screen candidate agents for activity as GPCR receptor agonists or antagonists.

In an exemplary embodiment, cells coexpressing a tetGα and a GPCR are pre-loaded with fluorescently-labeled calcium (e.g, fura-2). These cells are then exposed to a candidate GPCR binding compound and the effect of exposure to the compound monitored. Candidate compounds that have agonist activity are those that, when contacted with the tetGα- and GPCR- expressing cells, elicit a GPCR-mediated increase in intracellular calcium relative to control cells (e.g., tetGα and GPCR-expressing cells in the absence of the candidate com.pound, host cells without GPCR-encoding nucleic acid, GPCR-expressing cells exposed to a known GPCR agonist). Similarly, functional assays can be used to identify candidate compounds that block activity of a known GPCR agonist (e.g., block the activity of or compete with a known agonist), block activity of a known GPCR antagonist (e.g., block the activity of or compete with a known antagonist).

A number of G-protein coupled receptors have been shown to exhibit activity in the absence of agonist (so-called spontaneous or basal activity). This agonist-independent basal activity can be inhibited by compounds previously considered to be antagonists (e.g., the antipsychotic drugs). Therefore, these compounds are inverse agonists rather than antagonists. For example, very little β2 adrenoceptor-stimulated GTPγS binding was observed even with a large excess of $G_s\alpha$. However, both basal and isoproterenol-stimulated GTPγS binding were dramatically increased in membranes expressing tetG$_s\alpha$.

As many more GPCRs with constitutive activity are found (including native as well as mutated receptors), a newly recognized class of drugs termed inverse agonists are becoming increasingly important therapeutic agents. Inverse agonism is demonstrated when a drug binds to a receptor that exhibits constitutive activity and reduces this constitutive activity.

The assays of the present invention using the modified Gα. are particularly well suited to identify promising inverse agonists for specific receptors, as they provide a direct method for detecting a decrease in GPCR activity in response to a compound. In an exemplary assay, membranes or whole cells coexpressing tetGα and a target GPCR can be contacted with a candidate inverse agonist, and the activity of the G protein activation measured, e.g., by measuring GTPase activity, binding of GTP analogs, and/or activation of molecules such as AC. Compounds that decrease the basal activity of the receptor in the assay are identified as inverse agonists, and may then be subject to further testing for therapeutic use.

The assay preferable for identifying inverse agonists is the measurement of AC, as an inverse agonist response on AC levels is generally greater in the tetGα system than an agonist response (See FIGS. 33–37). The measurement of AC is thus particularly effective at the identification of ligands that can decrease basal GPCR activity level, allowing direct identification of this class of compounds.

Other measurements of G protein activation, such as measurement of Inositol-3-phosphate and/or and kinase activity, will also be apparent to one skilled in the art upon reading the present disclosure.

Identification of Ligands for Orphan GPCRs

An assay system according to the invention can also be used to classify compounds for their effects on G protein coupled receptors, such as on orphan receptors, to identify candidate ligands that are the native ligands for these orphan receptors. Membranes expressing the orphan receptors and a tetGα can be exposed to a series of candidate ligands, and the ligands with the ability to activate signaling through the receptors can be identified through G protein activation, e.g., by measuring GTPase activity, binding of GTP analogs, or binding and/or activation of AC.

Assays to Determine the Presence of a GPCR-activating Chemical in a Sample

The present invention also provides a rapid and reliable method for determining G protein activation through receptors known to be involved in drug responses. The present invention thus can also be used to test for drugs, e.g., narcotics, e.g., cocaine, heroin, morphine or designer opiates in foods or bodily fluids, e.g., blood or urine. An exemplary assay for identifying a drug in a substance (e.g., an opioid) would comprise the steps of contacting membranes expressing a GPCR (e.g., an opioid receptor) and an appropriate tetGα with a sample suspected of containing the drug. The presence of the drug can be verified by detecting, either qualitatively or quantitatively, the activity of G protein signaling in the membranes. This activation can be measured, e.g., by measuring GTPase activity, or binding and/or activation of AC, and increased activation of the G proteins is indicative of the presence of the drug in the sample.

Identification of GPCRs involved in Various Biological Processes

The GPCRs that are involved in biological responses, both normal responses (e.g., taste, smell, etc.) and pathological responses (e.g., the biological response to a GPCR involved in a disease or disorder) can be determined using assays of the invention. An assay using an array of membranes or cells, each sample of the array coexpressing a tetGα subunit and a particular GPCR, can be exposed to the stimulus (e.g., the odor, flavor compound, disease related complex, and the like), and the activity of each sample of the array can be determined. This can identify multiple receptors in a highthroughput manner that are involved in the transduction of signals in response to the stimulus.

For example, the highthroughput assays of the invention can be especially useful in determining the spectrum of GPCRs, e.g., olfactory receptors, that are activated or inverse agonized by a specific substance or mixture of substances. For example, a liquid can be contacted with an array of membrane preparations coexpressing a tetGα subunit and a particular GPCR, and the GPCRs activated or suppressed can be identified.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1
Construction of a Membrane Tethered G Protein α-subunit and Expression in Cell Culture To investigate the functional significance of $G_s\alpha$ dissociation from the plasma membrane following receptor activation, a membrane tethered form of $G_s\alpha$ (tet$G_s\alpha$) was constructed by fusing the amino-terminus of $G_s\alpha$ to the carboxyl-terminus of a single membrane-spanning region of a protein. The single membrane-spanning protein was made by fusing the amino-terminal 64 amino acids of the β2 adrenoceptor to its carboxyl-terminal 70 amino acids. Specifically, DNA sequences encoding amino acids 1–64 of the β2 adrenoceptor (Gether, U. et al., (1995) *J. Biol. Chem.* 270, 28268–75; Kobilka, B. K. (1995) *Anal. Biochem.* 231: 269–71; Gether, U. et al., (1997) *J. Biol. Chem.* 272:2587–90) were fused with amino acids 343–412 of the β2 adrenoceptor using a linker-adaptor. The linker-adaptor encoded the amino acid sequence TVTNYFR (SEQ ID NO:5) and connected the PstI site in the DNA sequence encoding the first cytoplasmic loop with the BanII site in the DNA sequence encoding the carboxyl-terminus. A cDNA encoding this β2-$G_s\alpha$ fusion protein was cloned into pVL1392, and digested with NcoI and EcoRV to remove the sequence encoding amino acids 1–370 of the β2 adrenoceptor. The NcoI-EcoRV fragment from the membrane anchor was ligated into the large NcoI-EcoRV fragment from pVL1392 β2 $G_s\alpha$ to produce tet$G_s\alpha$ in pVL1392 (FIG. 1).

Example 2
Coexpression of β2 AR and Either tet$G_s\alpha$ or $G_s\alpha$ in Sf9 Insect Cell Membranes To evaluate the consequence of restricting the mobility of $G_s\alpha$, β2 AR was expressed in Sf9 insect cells together with either tet$G_s\alpha$ (tet$G_s\alpha$ membranes), or $G_s\alpha$ ($G_s\alpha$ membranes). Constructs encoding either wild-type $G_s\alpha$ or tet $G_s\alpha$ were transfected into the Sf9 cells using a BaculoGold transfection kit (Pharmigen, San Diego, Calif.). Virus stocks were characterized by infecting Sf9 cells seeded at $3.0 \times 10^6$ cells/mL with dilutions ranging from 1:50 to 1:500 to determine the dilution that produced the highest expression of recombinant protein. Cells were incubated in a 27 C. shaker (125 rpm) for 48 h.

For coexpression studies, a series of Sf9 cell cultures (100–200 mL) were infected with a 1:500 dilution of a high titer β2 adrenoceptor baculovirus stock and a 1:200–1:500 dilution of a high titer $G_s\alpha$ or tet$G_s\alpha$ baculovirus stock in order to achieve a desired receptor to G protein stoichiometry. Cultures having the desired expression levels of receptor and G protein were selected for study. Membranes were prepared as described previously (Seifert, R. et al., (1998) *J. Biol. Chem.* 273: 5109–16; Seifert, R. et al., (1998) *Eur. J. Biochem.* 255: 369–382). All of the β2AR coexpression studies comparing $G_s\alpha$ and tet$G_s\alpha$ were done with the same batch of membranes.

To confirm expression of these constructs in the cells, the $G_s\alpha$ or tet$G_s\alpha$ was detected via Western blot using an anti-$G_s\alpha$ antibody (Calbiochem, San Diego, Calif.) which recognized an epitope present on both tet$G_s\alpha$ and $G_s\alpha$. The approximate molecular masses of $G_s\alpha$ and tet$G_s\alpha$ were shown to be 52 and 70 kDa in the respective cultures. The mobility of tet$G_s\alpha$ is consistent with the known molecular mass of $G_s\alpha$ (52 kDa) and the predicted molecular mass of the membrane-tether (18 kDa). The level of level of $G_s\alpha$ in the Sf9 cells was approximately 10-fold higher than that of tet$G_s\alpha$ by densitometric quantitation.

The expression level of the β2 adrenoceptor is similar in the membrane preparations from the two cultures as shown by Western blot analysis and [$^3$H]DHA binding (Amersham, Arlington Heights, Ill.) (7.4 pmol/mg in $G_s\alpha$ membranes; 4.8 pmol/mg in tet$G_s\alpha$ membranes). The tet$g_s\alpha$ and the β2 adrenoceptor are both tagged at the amino-terminus with the FLAG epitope, and their expression was also examined using an M1 monoclonal antibody. Based on immunoreactivity with the M1 antibody, tet$G_s\alpha$ expression level is comparable to that of β2 adrenoceptor. Thus, in $G_s\alpha$ membranes, $G_s\alpha$ is approximately 10 times more abundant than the β2 adrenoceptor. Immunoreactive bands corresponding to the β2 adrenoceptor, $G_s\alpha$, or tet$G_s\alpha$ were not detected in uninfected cells with either anti-$G_s\alpha$ or M1 monoclonal antibody.

Example 3
Agonist-Stimulated $G_s\alpha$ and tet$G_s\alpha$ Release from Sf 9 Membranes GTP-sensitive, high-affinity agonist binding reflects the formation of the ternary complex between agonist, receptor, and guanine nucleotide-free G protein. $G_s\alpha$ has been observed to translocate from the plasma membrane to the cytoplasm following receptor activation in several mammalian cell lines. This phenomenon is also observed in Sf9 membranes expressing wild-type $G_s\alpha$ upon agonist binding, but not in membranes expressing tet$G_s\alpha$. Only a small fraction of $G_s\alpha$ is released following incubation with isoproterenol plus GTP, with GTPγS alone, or with GTPγS plus isoproterenol.

Figure 2:
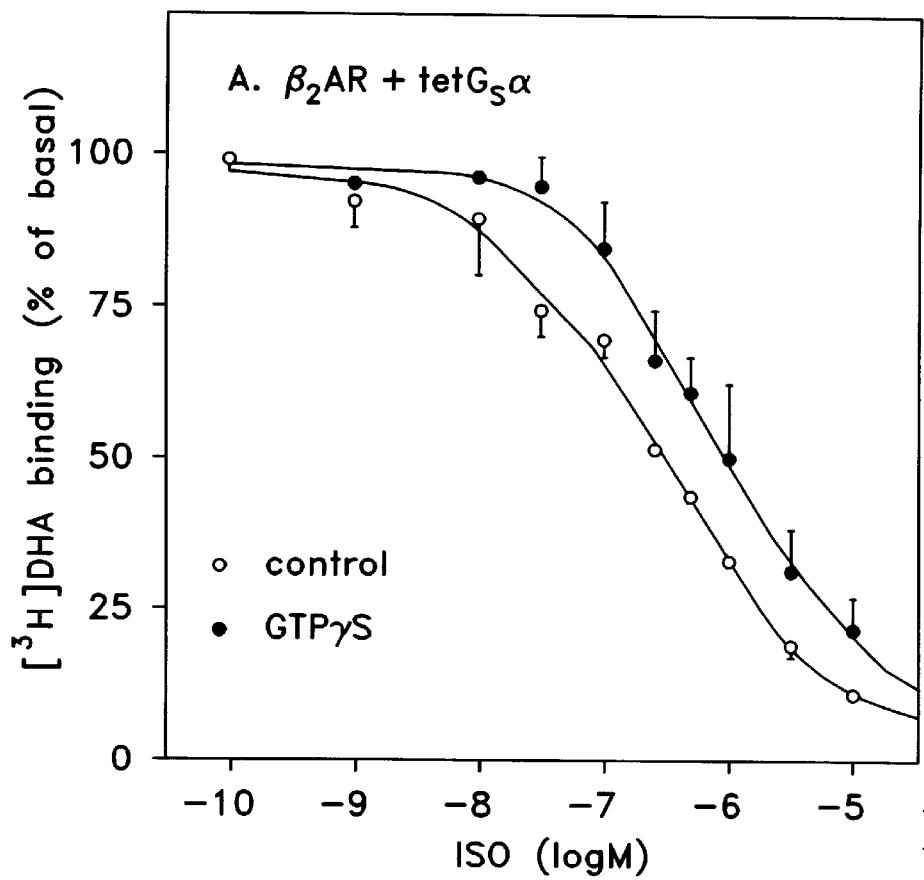
FIGS. 2 and 3 are a pair of graphs illustrating [$^3$H]DHA competition binding in Sf9 membranes coexpressing β2 adrenoceptor and $G_s\alpha$ (FIG. 2) or $tetG_s\alpha$ (FIG. 3). This was performed in the absence (○) or presence (●) of 10 μM GTPγS.
Figure 3:
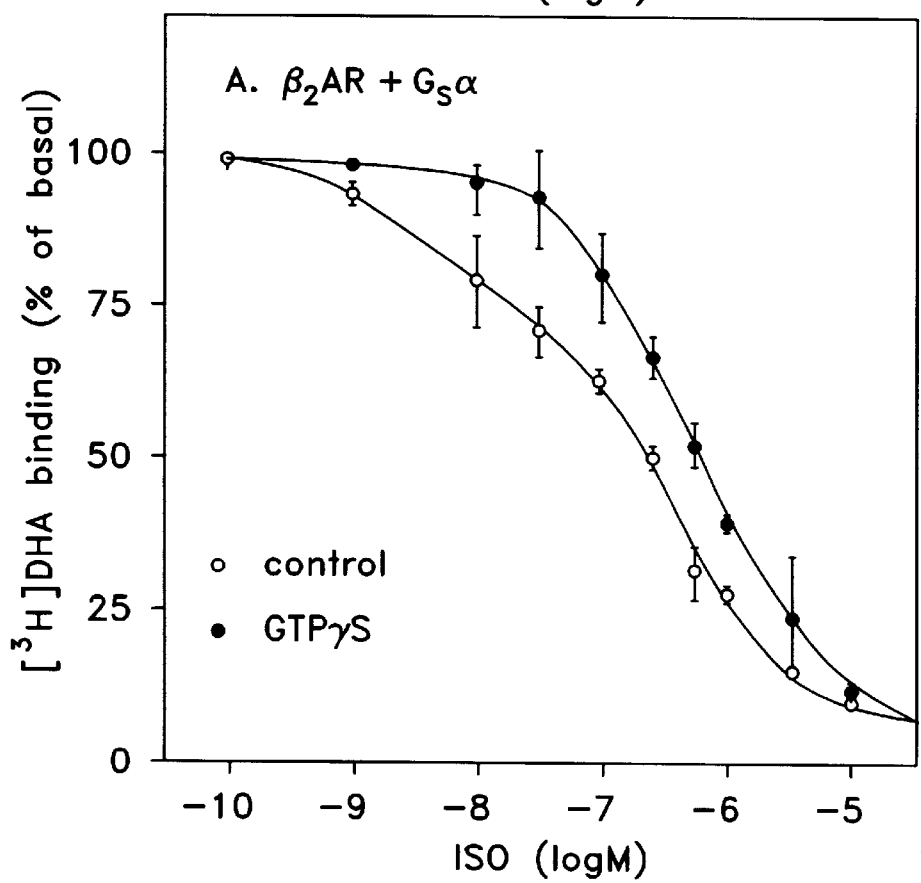

Competition binding of [$^3$H]DHA (1 nM) with varying concentrations of isoproterenol in Sf9 membranes coexpressing β2 AR and either wild-type $G_s\alpha$ (FIG. 2) or tet$G_s\alpha$ (FIG. 3). Membrane proteins (15–20 μg/tube) from infected Sf9 insect cells were suspended in 500 μL of binding buffer (75 mM Tris/HCl, pH 7.4, 12.5 mM MgCl2, and 1 mM EDTA), supplemented with 10 nM [$^3$H]DHA and 0.2% (w/v) BSA to determine β2 adrenoceptor expression level. Nonspecific binding was assessed in the presence of 10 μM (−)-alprenolol. Incubations were performed for 60 min at 25° C. with shaking at 200 rpm. Competition binding experiments were carried out with 1 nM [$^3$H]DHA in the presence of isoproterenol at various concentrations without or with GTPγS (10 μM) as described elsewhere (Seifert, R. et al., (1998) *J. Biol. Chem.* 273: 5109–16; Seifert, R. et al., (1998) *Eur. J. Biochem.* 255: 369–382). Expression levels of β2 adrenoceptor in FIGS. 2 and 3 are 7.4 and 4.8 pmol/mg, respectively. Data are expressed as percent of basal bound [$^3$H]DHA. Data shown are the mean ±SD of three independent experiments performed in triplicate.

β2 AR has previously been shown to couple poorly to endogenous insect cell G proteins, i.e., no GTPγS sensitive, high-affinity binding is observed in the absence of coexpressed mammalian $G_s\alpha$ (Seifert, R. et al., (1998) *J. Biol. Chem.* 273: 5109–16; Seifert, R. et al., (1998) *Eur. J. Biochem.* 255: 369–382). As shown in FIGS. 2 and 3, GTPγS -sensitive high-affinity binding of the agonist isoproterenol was observed in both $G_s\alpha$ and tet$G_s\alpha$ membranes. Approximately 30% GTPγS -sensitive high-affinity agonist binding sites were observed for the β2 AR in both $G_s\alpha$ and tet$G_s\alpha$ expressing membranes. This was surprising since the ratio of G protein to receptor (moles of $G_s\alpha$ per moles of β2 adrenoceptor) was about 10 in $G_s\alpha$ membranes and about 1 in tet$G_s\alpha$ membranes.

Example 4
Agonist-Stimulated $G_s\alpha$ and tet$G_s\alpha$ Release from Membranes Coexpressing β2 AR The basal and agonist-stimulated GTPase activity in Sf9 membranes expressing β2 adrenoceptor and either $G_s\alpha$ or tet$G_s\alpha$ was then examined. GTPase activity measures the velocity of the complete G protein cycle.

For construction of dose response curves to ligands, assay tubes (100 μL) containing 10 μg of membrane protein, 0.1 μM [γ-$^{32}$P]GTP (0.1 iCi/tube) (NEN-DuPont, Boston, Mass.), 1.0 mM $MgCl_2$, 0.1 mM EDTA, 0.1 mM ATP, 1 mM adenylyl imidodiphosphate, 5 mM creatine phosphate, 40 μg of creatine kinase, and 0.2% (w/v) BSA in 50 mM Tris/HCl, pH 7.4 were contacted with ligand. Reaction mixtures contained ligands at 1 μM to 1 mM as determined from saturated dose response curves: isoproterenol (10 μM), salbutamol (100 μM), dobutamine (100 μM), ephedrine (1 mM), dichloroisoproterenol (100 μM), and alprenolol (1 μM) were used.

Reactions were performed for 20 min at 25 C. and were terminated by the addition of 900 μL of a slurry consisting of 5% (w/v) activated charcoal and 50 mM NaH2-PO4, pH 2.0, as described elsewhere ((Seifert, R. et al., (1998) *J. Biol. Chem.* 273: 5109–16). Reaction mixtures were centrifuged for 15 min at room temperature at 15000 g. 700 μL of the supernatant of reaction mixtures were transferred, and [$^{32}$P]Pi was determined by liquid scintillation counting.

Figure 4:
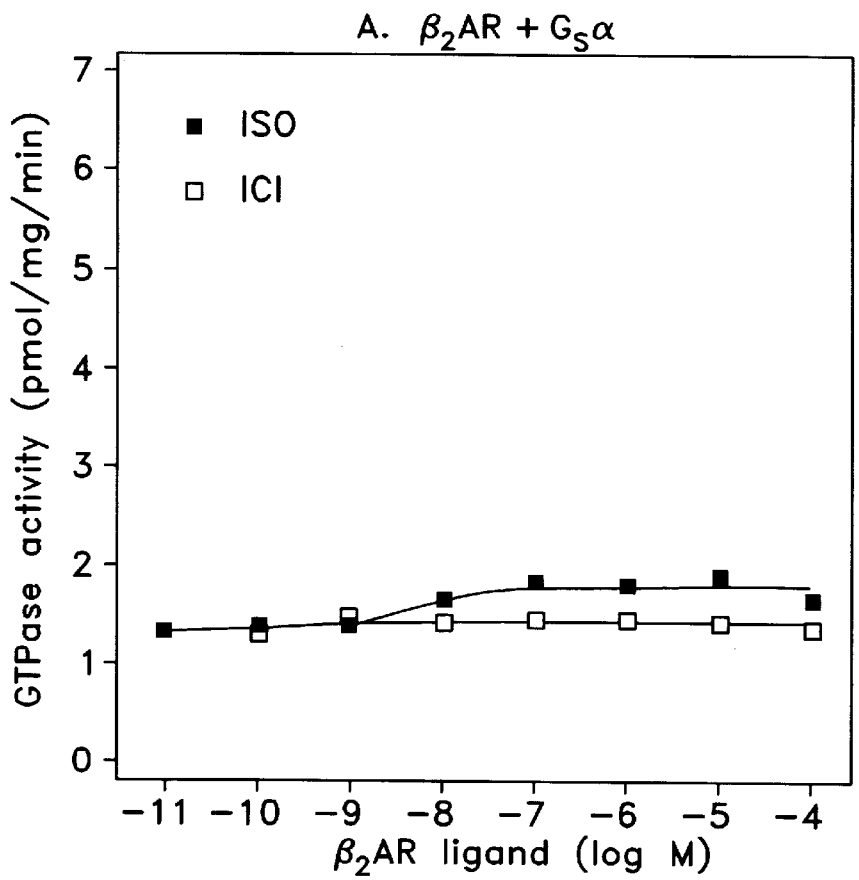
FIGS. 4 and 5 are a pair of graphs comparing the ligand regulation of GTPase activity in membranes coexpressing β2 adrenoceptor and $G_s\alpha$ (FIG. 4), or $tetG_s\alpha$ (FIG. 5). GTP hydrolysis was measured with 100 nM [γ-$^{32}$P]GTP as substrate in the presence of isoproterenol (●) or ICI-118551 (○) in membranes (10 μg of protein) coexpressing β2 adrenoceptor (7.4 pmol/mg) with $G_s\alpha$ and β2 adrenoceptor (4.8 pmol/mg) with $tetG_s\alpha$. Data shown are the means (SD of three independent experiments performed in triplicate.
Figure 5:
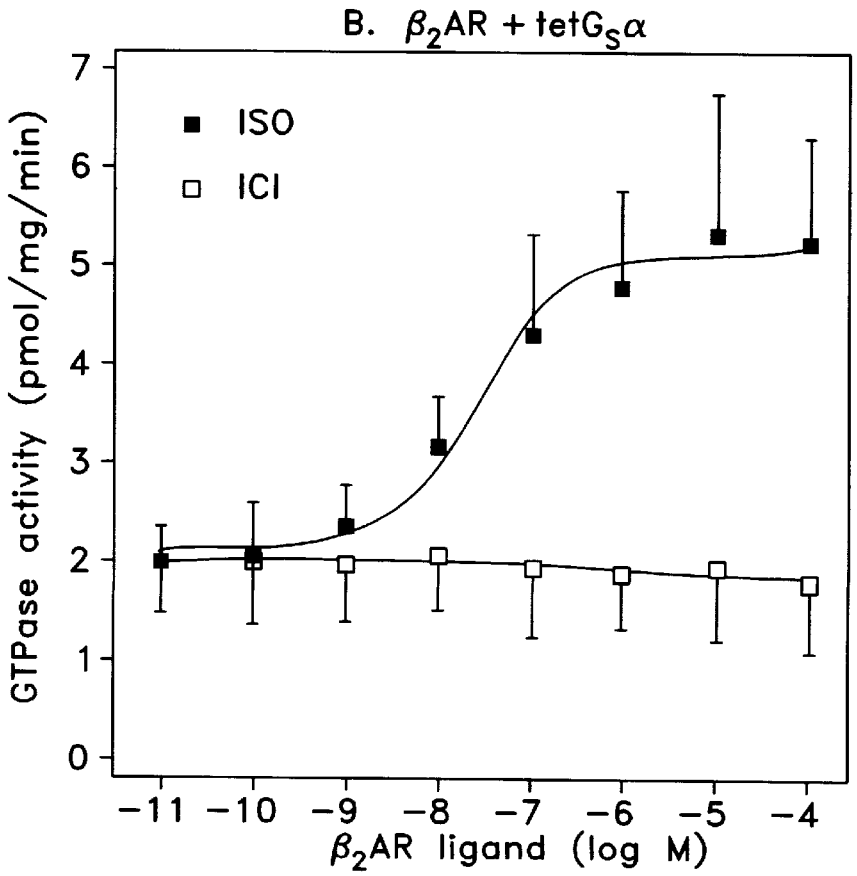

The intrinsic activities of ligands at β2 adrenoceptor in $G_s\alpha$ membranes were plotted against their intrinsic activities at β2 adrenoceptor in tet$G_s\alpha$ membranes. There was a modest (1.6-fold) elevation of basal GTPase activity in tet$G_s\alpha$ membranes (FIG. 5) compared to $G_s\alpha$ membranes (FIG. 4); however, isoproterenol-stimulated GTPase activity in tet$G_s\alpha$ membranes was 2.8-fold higher than the activity in $G_s\alpha$ membranes. There was no significant response to the inverse agonist ICI-118551 for either membrane preparation. GTPγS binding in Sf9 membranes was performed in the presence of 1 μM GDP to reduce the background binding of GTPγS to endogenous insect cell G proteins. Data shown are the mean±SD of three independent experiments performed in triplicate.

Figure 6:
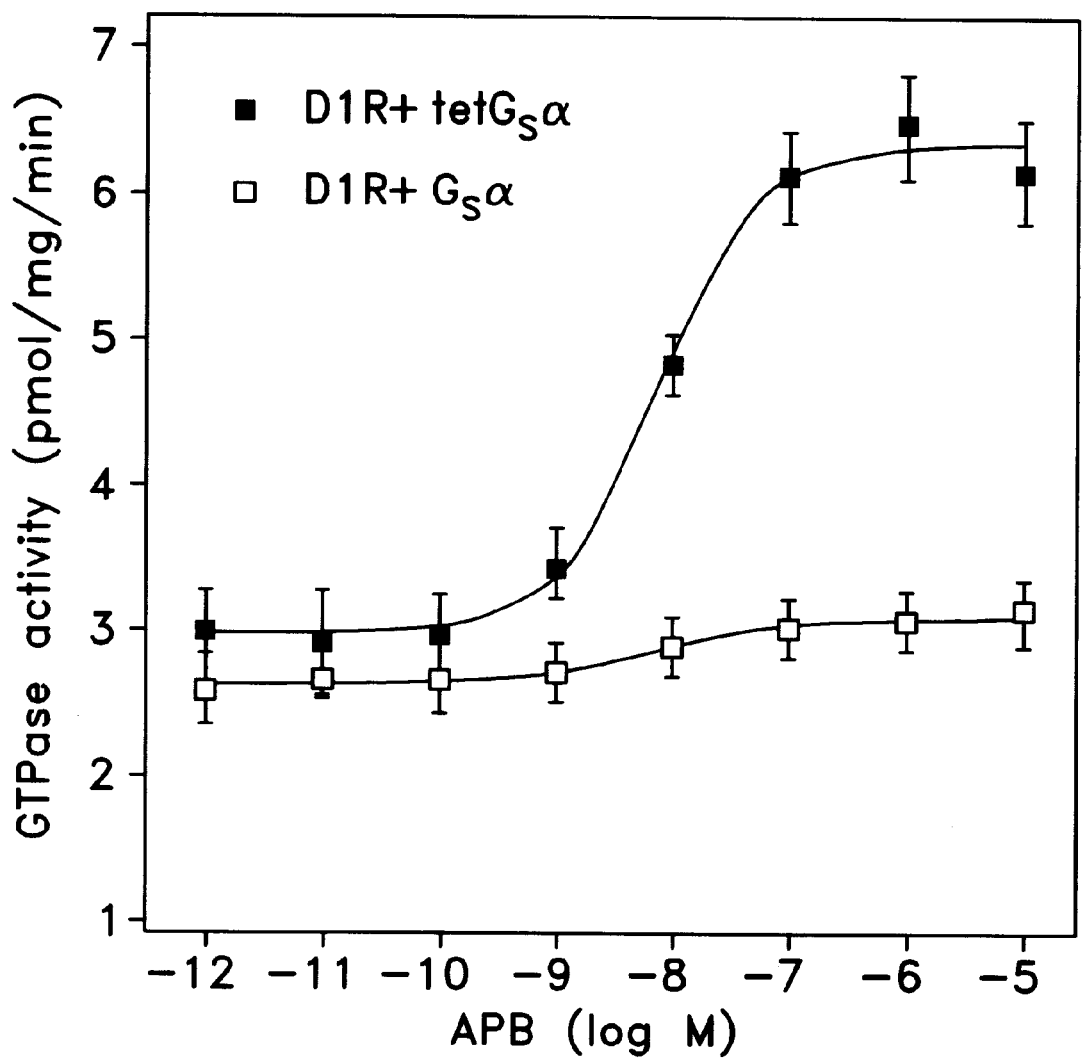
FIG. 6 is a graph illustrating the ligand regulation of GTPase activity in membranes coexpressing D1 dopamine receptor and $G_s\alpha$ or $tetG_s\alpha$.

Regulation of G protein activity by the D1 dopamine receptor was also determined in membranes coexpressing D1 dopamine receptor and either $G_s\alpha$ or tet$G_s\alpha$. GTP hydrolysis was measured with 100 nM [γ-$^{32}$P]GTP as substrate in the presence of chloro-APB hydrobromide (APB) in membranes (10 μg of protein) coexpressing D1 dopamine receptor (4.9 pmol/mg) with $G_s\alpha$, and D1 dopamine receptor (5.0 pmol/mg) with tet$G_s\alpha$ (FIG. 6). The ligand-stimulated activity in tet$G_s\alpha$ membranes was also higher than the activity in $G_s\alpha$ membranes. Data shown are the mean±SD of three independent experiments performed in triplicate.

Example 5
GTPγS Binding in Membranes Coexpressing β2 AR and $G_s\alpha$ or tet$G_s\alpha$ GTPγS binding measures the uptake of the nonhydrolyzable GTP analogue GTPγS to the α-subunit and is therefore not a steady-state assay (1, 23). However, this assay provides information about the number of G proteins accessible to receptors during a given period of time (1, 23). Thus, GTPγS binding was carried out in tet$G_s\alpha$ and $G_s\alpha$ membranes coexpressing either β2 AR or the D1 dopamine receptor. The expression levels of tet$G_s\alpha$ and $G_s\alpha$ in cells expressing the D1 receptor are similar to the level of tet$G_s\alpha$ in cells expressing the β2AR.

Membranes were pelleted by a 15 min centrifugation at 4 C. and 15000 g and resuspended in binding buffer. Sf9 membranes (10 μg of protein/tube) were suspended in 500 μL of binding buffer supplemented with 0.05% (w/v) BSA, 1 nM [$^{35}$S]GTPγS (0.25 uCi/tube), GDP (1 μM) with or without isoproterenol (10 μM). Incubations were performed at 25 C. and shaking at 200 rpm. Nonspecific binding was determined in the presence of 10 μM GTPγS and was less than 0.2% of total binding. Bound [$^{35}$S]-GTPγS was separated from free [$^{35}$S]GTPγS by filtration through GF/C filters, followed by three washes with 3 mL of cold binding buffer. Filter-bound radioactivity was determined by liquid scintillation counting.

Figure 7:
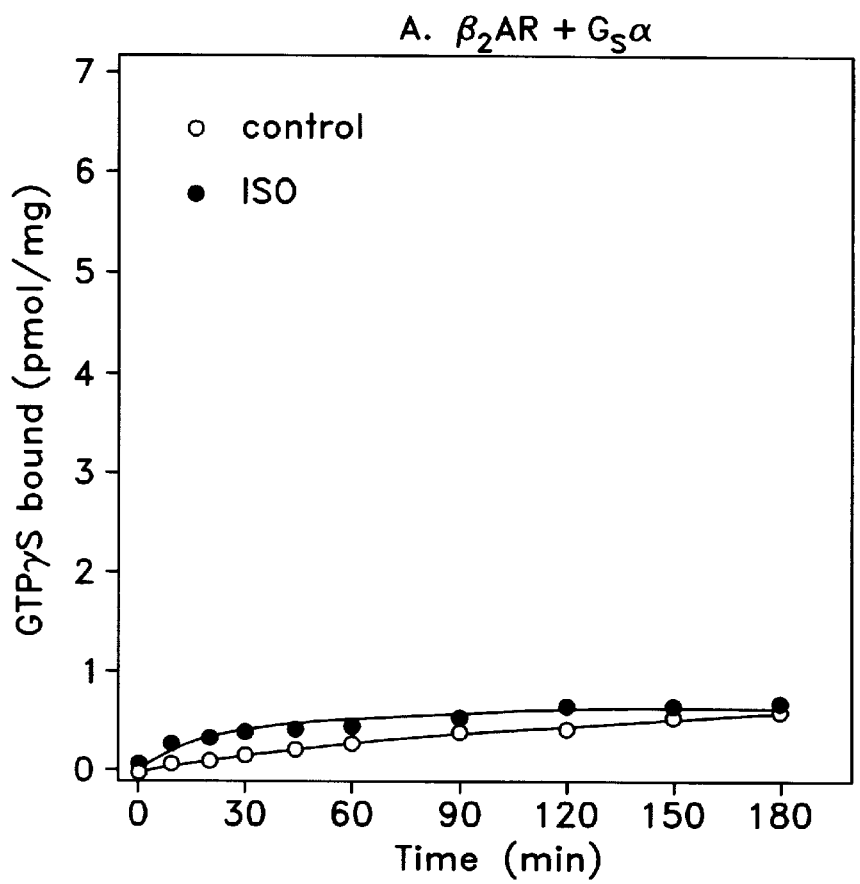
FIGS. 7 and 8 are a pair of graphs showing a time course of [$^{35}$S]GTPγS binding in membranes coexpressing β2 AR and $G_s\alpha$ (FIG. 7) or $tetG_s\alpha$.
Figure 8:
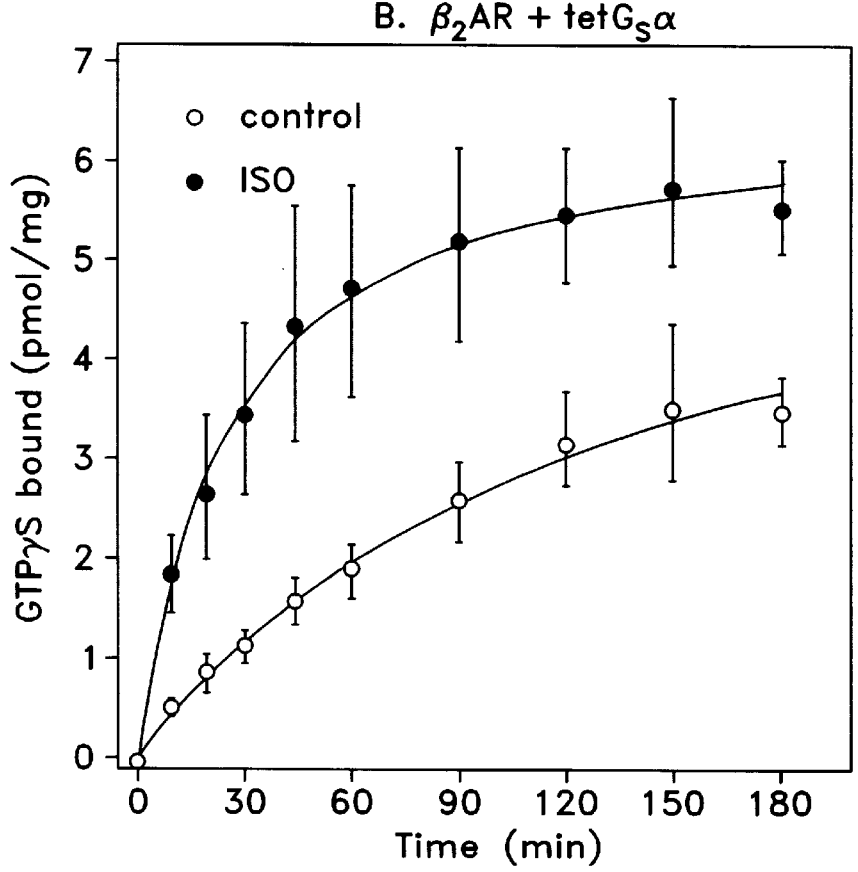
Figure 9:
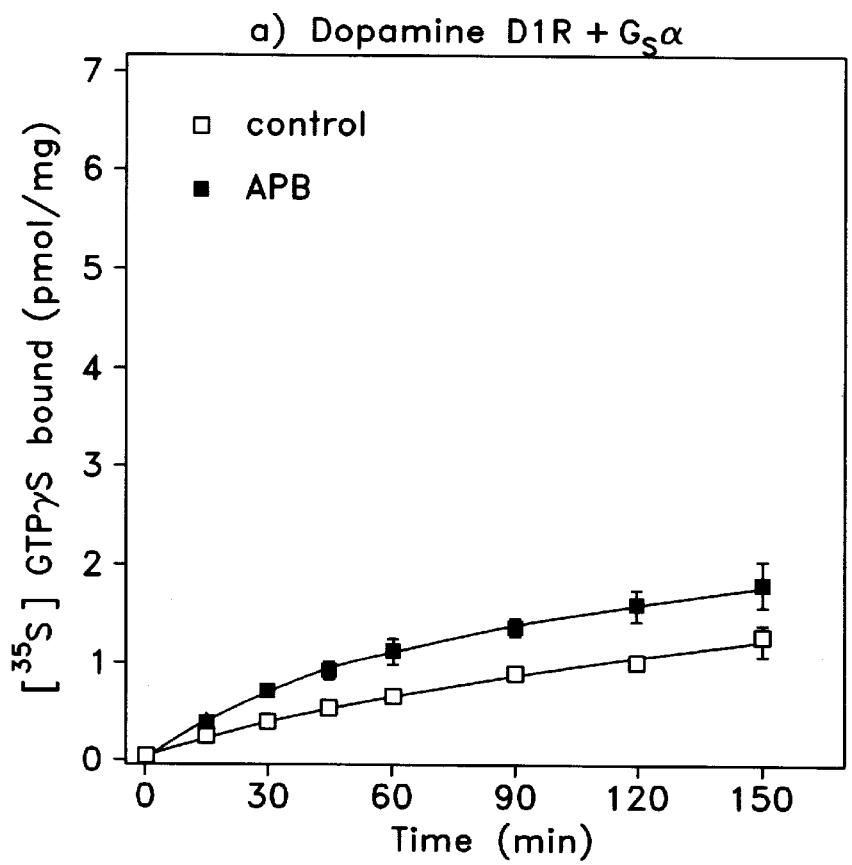
FIGS. 9 and 10 are graphs illustrating the time course of [$^{35}$S]GTPγS binding in membranes coexpressing D1 dopamine receptor and $G_s\alpha$ (FIG. 9) or $tetG_s\alpha$ (FIG. 10).
Figure 10:
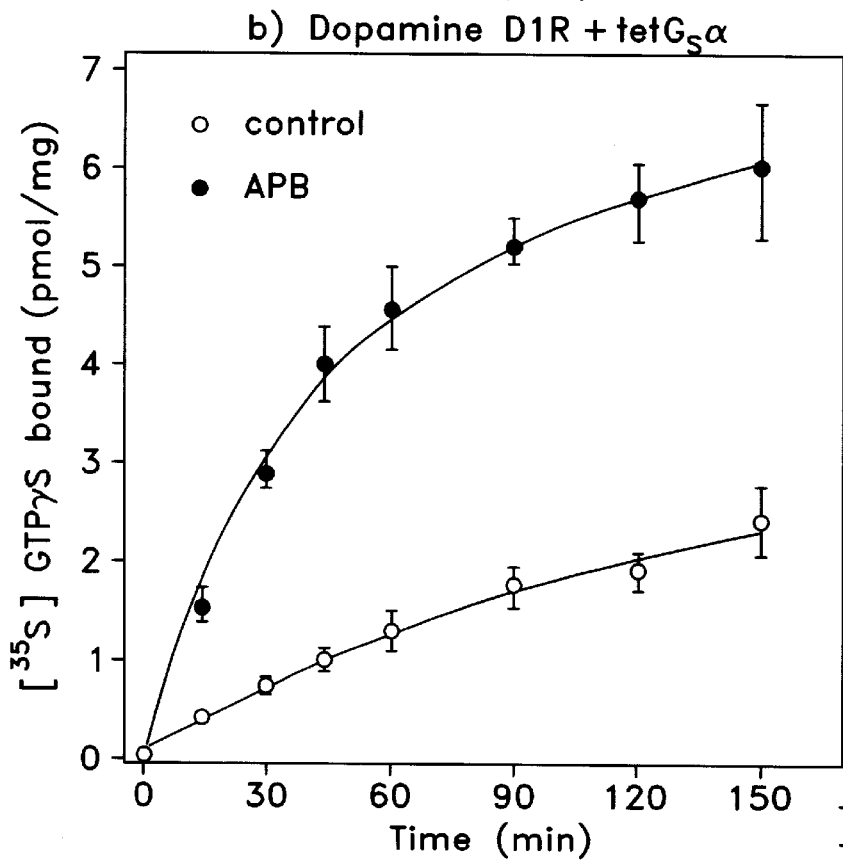

Surprisingly, both basal and isoproterenol-stimulated GTPγS binding were much higher in tet$G_s\alpha$ membranes expressing β2 AR than in $G_s\alpha$ membranes expressing β2 AR, even though the tet$G_s\alpha$ membranes had a lower G protein expression level than $G_s\alpha$ membranes (FIGS. 7 and 8). Efficient coupling with tet$G_s\alpha$ is also not limited to the β2 AR. Basal and agonist-stimulated GTPγS binding and GTPase activity were both significantly greater in membranes expressing the D1 dopamine receptor and tet$G_s\alpha$ than in membranes expressing the D1 dopamine receptor and wild-type $G_s\alpha$ (FIGS. 9 and 10). In these experiments, tet$G_s\alpha$ and $G_s\alpha$ were expressed at similar levels as determined by Western Blot analysis. Expression levels of D1 dopamine receptor in FIGS. 9 and 10 are 4.9 and 5.0 pmol/mg, respectively. Data shown are the mean±SD of three independent experiments performed in triplicate.

Example 6
Reversal of Membrane Localization of tet$G_s\alpha$ by Site Specific Cleavage The efficient coupling observed with tet$G_s\alpha$ could reflect differences in the processing of a tethered $G_s\alpha$ during biosynthesis in Sf9 cells. To test this hypothesis, a cleavable form of tet$G_s\alpha$ (TEVtet$G_s\alpha$) in which the carboxyl-terminus of the membrane tether is separated from the amino-terminus of $G_s\alpha$ by a cleavage site for Tobacco Etch Virus (TEV) protease was generated.

To construct TEV-tet$G_s\alpha$, a sequence of 27 base pairs (ACT AGT GAA AAT CTT TAT TTC CAG GGA (SEQ ID NO:10)) encoding a Tobacco Etch Virus (TEV) protease cleavage site was inserted between the sequence encoding the membrane tether and the sequence encoding the amino-terminus of $G_s\alpha$, by overlap-extension PCR. This construct was transfected into Sf9 cells as described in Example 2. Western detection of TEV protease treated-TEV-tet$G_s\alpha$ in Sf9 membranes (50 μg) with anti-$G_s\alpha$ antibody (1:1000) confirmed expression of the protein in these cells.

Isoproterenol stimulated GTP hydrolysis was measured as described in Example 4 in membranes with or without TEV protease treatment. TEV protease efficiently cleaved $G_s\alpha$ from the membrane tether, and dramatically reduced the efficiency of coupling to the β2 adrenoceptor as determined by GTPase activity (FIG. 11) and GTPγS binding (FIGS. 12 and 13). Thus, it appears that $G_s\alpha$ released from TEVtet$G_s\alpha$ following TEV cleavage is not functionally superior to wild-type $G_s\alpha$ expressed in insect cells.

Figure 11:
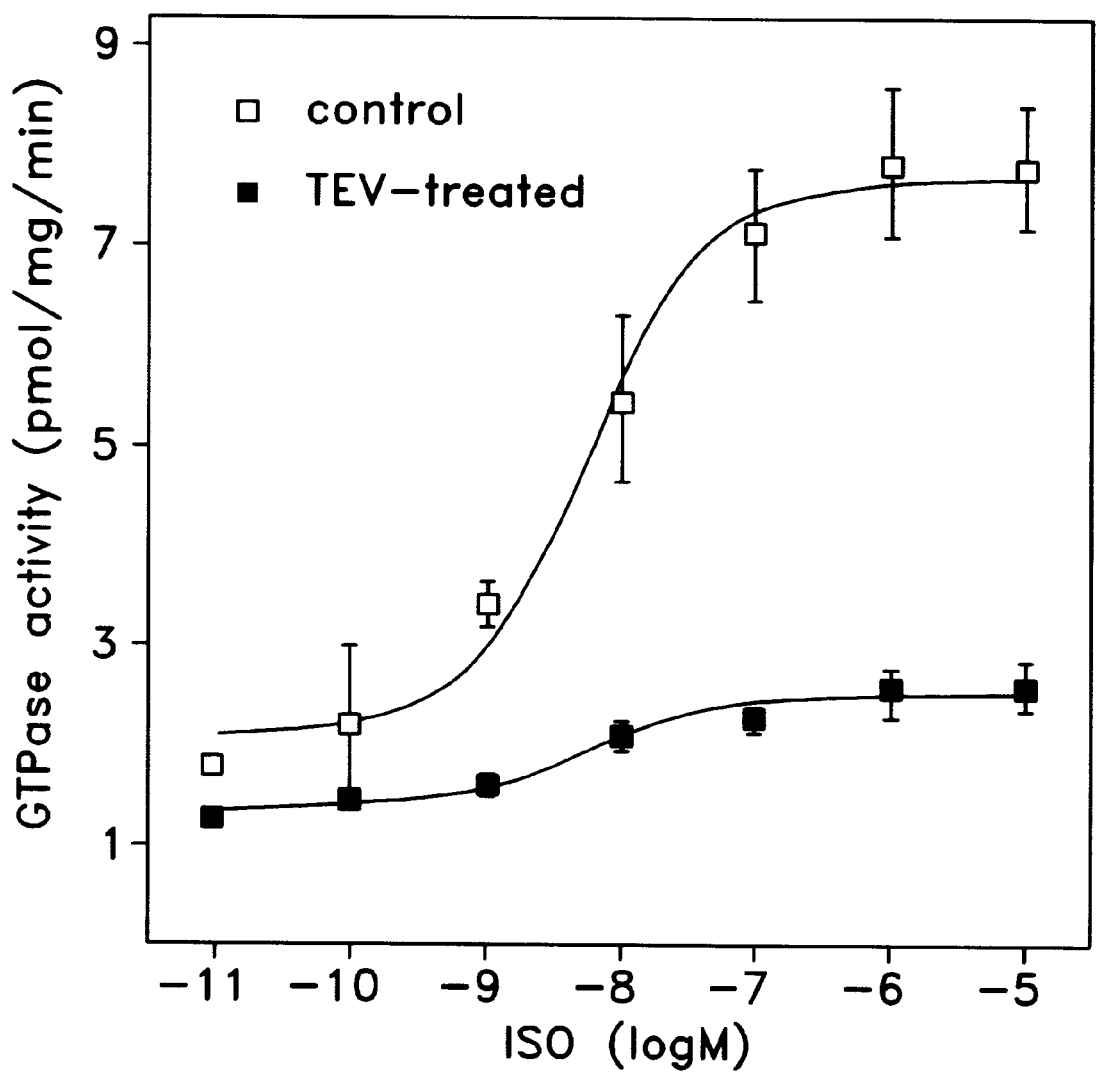
FIG. 11 is a graph illustrating the reversal of membrane tethering by site-specific TEV cleavage.
Figure 12:
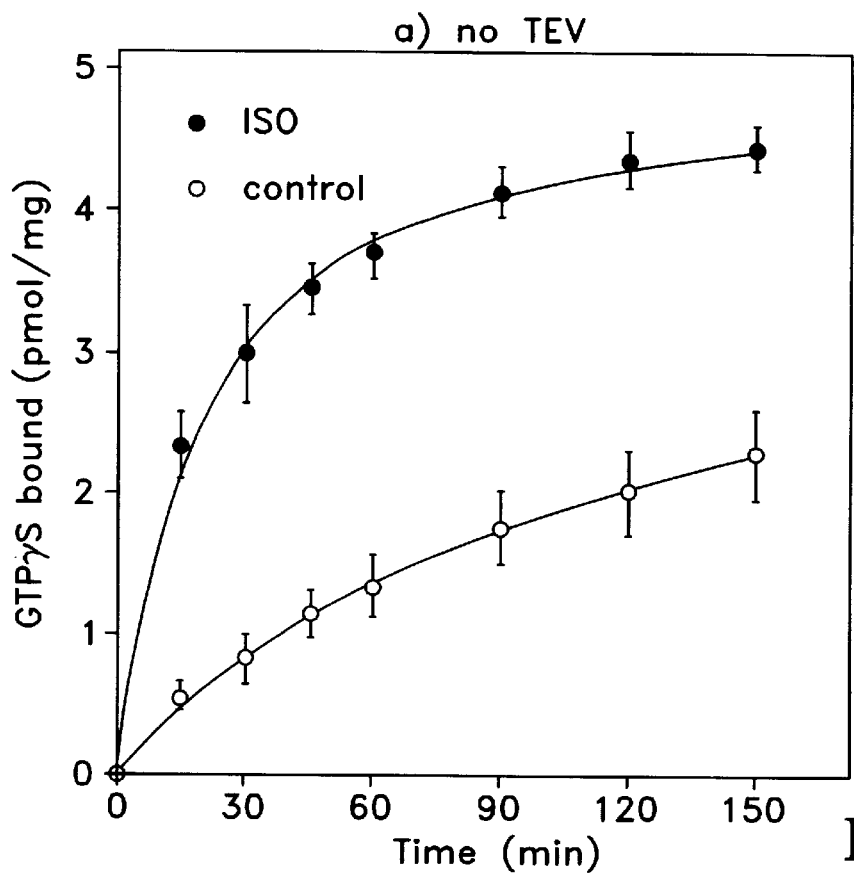
FIGS. 12 and 13 illustrate [$^{35}$S]GTPγS binding in the absence (○) or presence (●) of 1 μM isoproterenol (ISO) without (FIG. 12) or with (FIG. 13) TEV protease treatment for 30 min at room temperature.
Figure 13:
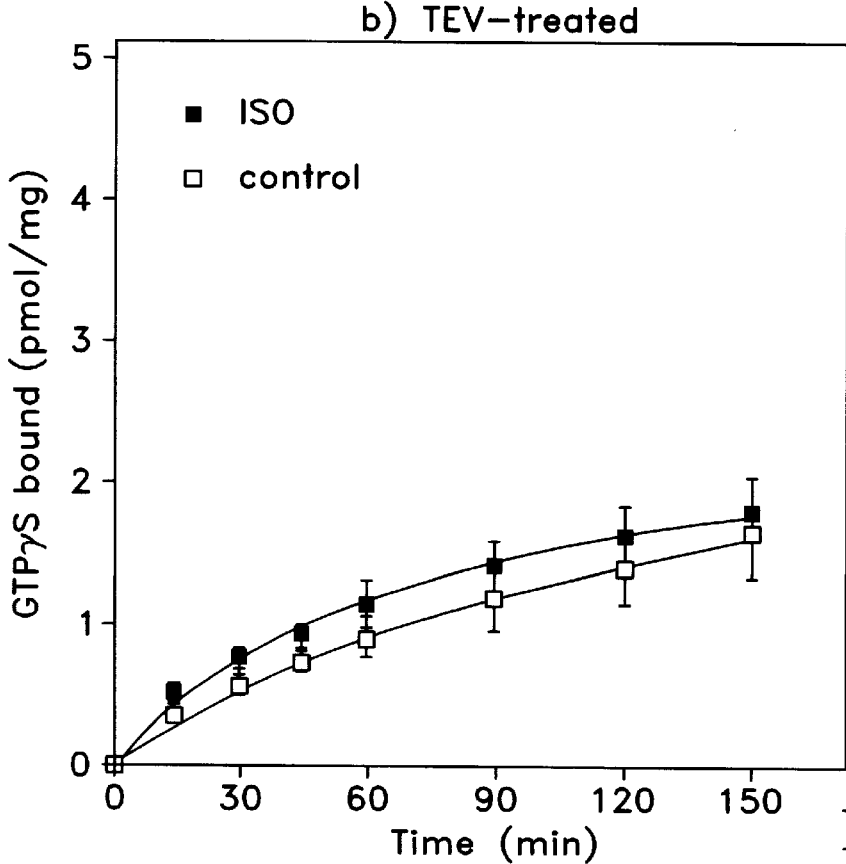

As shown in FIGS. 11–13, TEV cleavage dramatically reduces coupling of receptor to $G_s\alpha$ as determined by GTPase activity and GTPγS binding. In contrast to the experiments shown in previous figures, the levels of receptor, AC and G protein are identical in the two membrane preparations, the only difference being cleavage of the membrane tether.

Example 7
Regulation of AC in Membranes Expressing tetG$_s$α or G$_s$α

The β2 adrenoceptor has been shown to couple inefficiently to insect cell AC via the insect cell Gs-like G protein. However, the coupling efficiency can be dramatically improved if mammalian G$_s$α is coexpressed in insect cells with the β2 adrenoceptor. Therefore, the basal and agonist-stimulated AC activity in membranes expressing G$_s$α and tetG$_s$α is largely due to the mammalian G protein.

Figure 14:
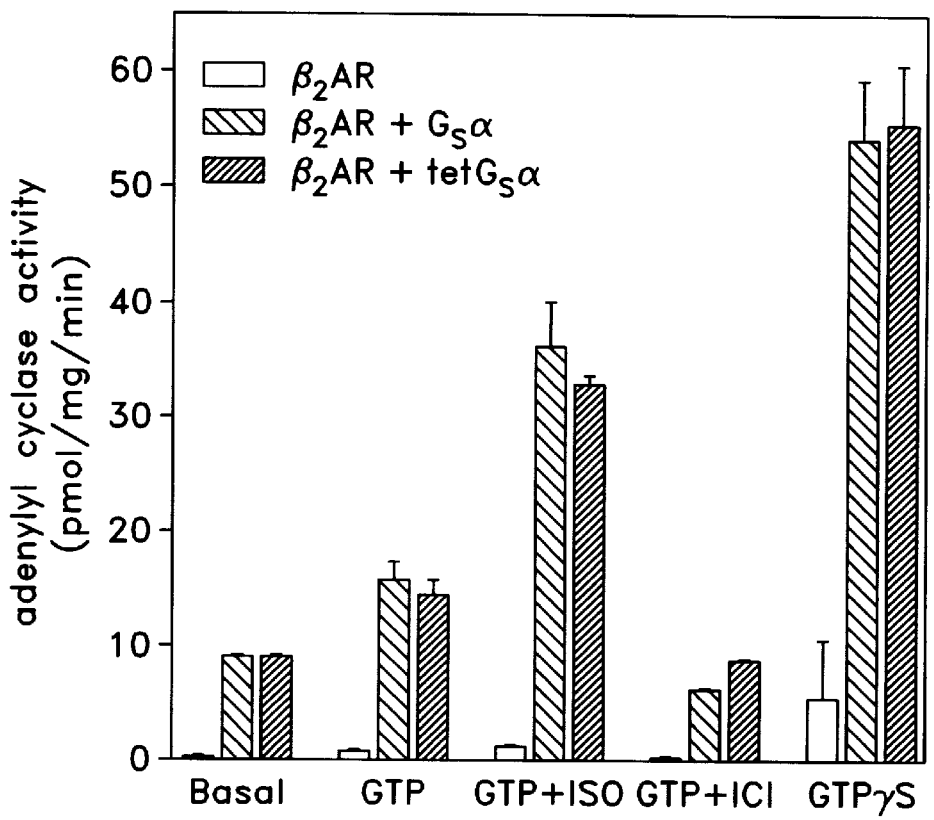
FIG. 14 is a bar graph illustrating the receptor-mediated activation of adenylyl cyclase (AC) through $G_s\alpha$ and through $tetG_s\alpha$.

AC activity was determined in membranes (20 μg) expressing β2 adrenoceptor alone or together with G$_s$α or tetG$_s$α : (a) basal, (b) 1 μM GTP, (c) 1 μM GTP plus 1 μM isoproterenol, (d) 1 μM GTP plus 1 μM ICI-118551, and (e) 1 μM GTPγS . Assay tubes (50 μL) contained: 15 μg of membrane protein, guanine nucleotides, and ligand as indicated in FIG. 14; 40 μM [α-$^{32}$ P]ATP (2.5 iCi/ tube) (NEN-DuPont, Boston, Mass.); 2.7 mM mono(cyclohexyl) ammonium phosphoenolpyruvate, 0.125 IU of pyruvate kinase, 1 IU of myokinase, 0.1 mM camp; 5 mM MgCl$_2$; 0.4 mM EDTA; and 30 mM Tris/HCl, pH 7.4. Reactions were conducted for 20 min at 37 C. Separation of [ $^{32}$P]cAMP from [α-$^{32}$ P]ATP was performed as described (Alvarez, R., and Daniels, D. V. (1990) *Anal. Biochem.* 187:98–103). The data shown in FIG. 14 are representative of four independent experiments (mean±SD). Similar results were produced with different membrane preparations.

In contrast to the results observed in GTPase and GTPγS binding assays, the β2 AR-stimulated AC in G$_s$α membranes and in tetG$_s$α membranes were similar. This is further confirmation that the G$_s$α component of tetgsa is not affected by the membrane tether.

Figure 15:
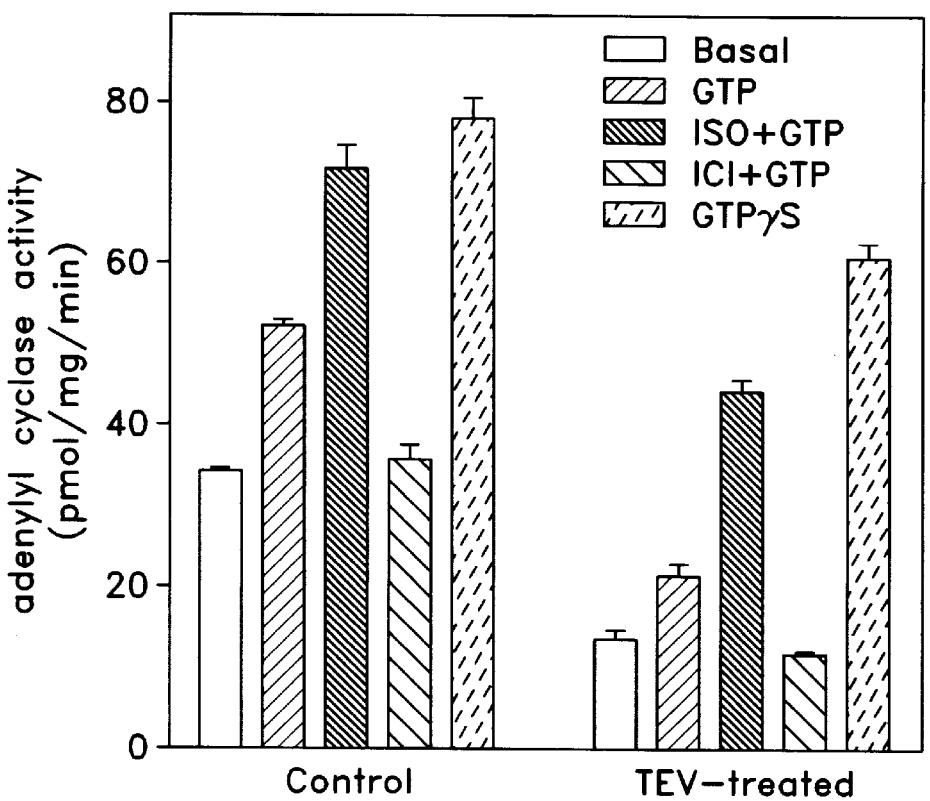
FIG. 15 is a bar graph illustrating AC activity in membranes expressing $tetG_s\alpha$ having a TEV cleavage site between the tethered portion and $G_s\alpha$.

AC activity was then determined in membranes expressing tetG$_s$α having a TEV cleavage site between the tethered portion and G$_s$α. Membranes were incubated with TEV or buffer control for 30 min at room temperature before performing AC experiments. As shown in FIG. 15, TEV cleavage has significant effects on basal and agonist activated AC.

Example 8
Intrinsic AC activities in Membranes Expressing tetG$_s$α or G$_s$α

Figure 16:
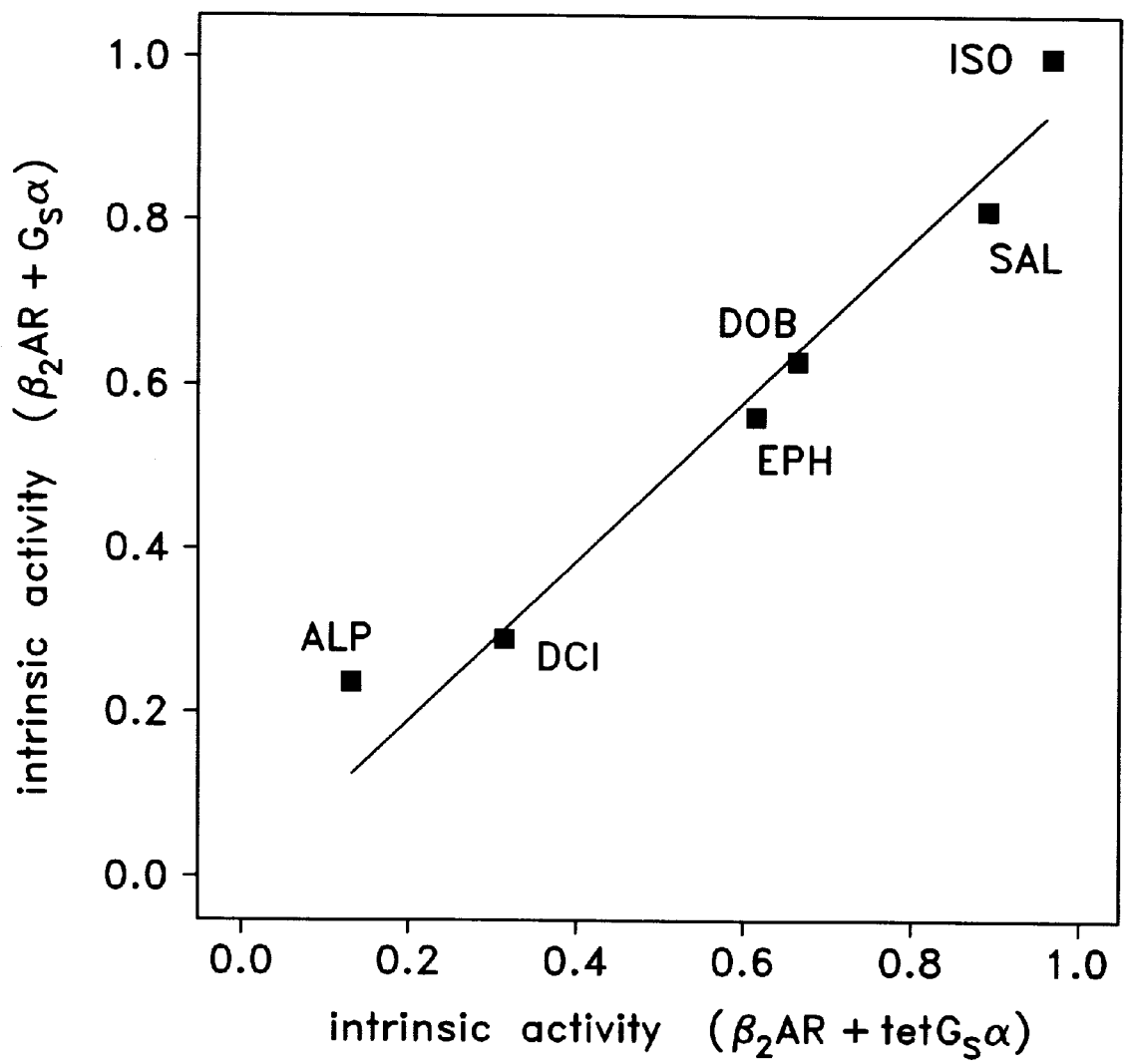
FIG. 16 is a line graph illustrating the intrinsic AC of full and partial β2 AR agonists.

AC activity was measured in the membrane proteins (20 μg) coexpressing β2 AR and G$_s$α or tetG$_s$α to determine intrinsic AC activities of full and partial β2 AR agonists in these membranes. AC was measured as described in Example 7. Reaction mixtures contained ligands at 1 μM to 1 mM as determined from saturated dose response curves: isoproterenol (10 μM), salbutamol (100 μM), dobutamine (100 μM), ephedrine (1 mM), dichloroisoproterenol (100 μM), and alprenolol (1 μM) were used. The intrinsic activities of ligands at β2 AR in G$_s$α membranes were plotted against their intrinsic activities at β2 AR in tetG$_s$α membranes (FIG. 16).

Example 9
Localization of G$_s$α and tetG$_s$α in the Membrane

Another possible explanation for the observed difference in the efficiency of coupling of G$_s$α and tetG$_s$α could be a difference in the distribution of these two proteins in cellular membrane compartments. Experiments shown in FIGS. 2–13 were performed on a crude membrane fraction that contains plasma membrane as well as intracellular membrane organelles. To examine the distribution of G$_s$α and tetG$_s$α in insect cell membranes, we fractionated whole-cell cell lysates (including cytosolic proteins) from Sf9 cells expressing either G$_s$α or tetG$_s$α in a discontinuous sucrose density gradient and subjected the fractions to Western blot analysis using anti-G$_s$α antibody.

For translocation studies, membranes (100–200 μg of protein/reaction) were resuspended in binding buffer containing various combinations of compounds (100 μM GTP, 100 μM isoproterenol, and 100 μM GTPγS). The membrane suspensions were incubated for 1 h at 37 C. After centrifugation at 150000 g for 30 min in Beckman TL 100, the supernatant fractions were precipitated by 2% (w/v) deoxycholate/24% (w/v) trichloroacetic acid, and neutralized with 20 μL of 1M Tris base solution. Precipitated protein was then dissolved in 50 μL of Laemmli sample buffer and proteins were separated by 10% SDS-polyacrylamide gel electrophoresis. Proteins were transferred onto nitrocellulose membranes and blotted with anti-G$_s$α antibody (1:1000).

For subcellular fractionation, pellets of Sf9 cells infected with baculovirus encoding β2-AR and either tetG$_s$α or G$_s$α were homogenized in ice-cold buffer (20 mM Tris/HC1, pH 7.4, 3 mM MgCl2,1 mM EDTA), including protease inhibitor cocktail (Boehringer Mannheim) with 30–35 strokes. Two milliliters of homogenates (20–40 mg of total protein) was applied on top of the discontinuous sucrose density gradients consisting of 19, 23, 27, 31, 35, and 43%. (g/100 ml) sucrose in 20 mM Tris/HCl, pH 8.0, 3 mM MgCl2, 1 mM EDTA, and centrifuged for 30 min at 27 000 rpm in a Beckman SW28 rotor at 4 C. as described elsewhere (Svoboda, P. et al., (1993) *Biochem. J.* 295: 655—61). Fractions of 5 mL were collected, and proteins from 750 μL of each fractions were precipitated by 2% (w/v) deoxycholate/24% (w/v) trichloroacetic acid, and neutralized with 30 μL of 1 M Tris base solution. Precipitated protein was then dissolved in 70 μL of Laemmli sample buffer and separated by 10% SDS-polyacrylamide gel electrophoresis.

Previous studies (Svoboda, P. et al., (1993) *Biochem. J.* 295: 655–61) have shown that fraction 1 contains predominantly cytosolic proteins, fractions 2–3 contain light vesicles including endoplasmic reticulum, fractions 4–6 contain plasma membranes, fraction 7 contains mitochondria, and fraction 8 is the pellet containing unbroken cells and nuclei. A significant amount of G$_s$α was observed in the lowest density fraction representing cytosolic proteins (fraction 1 and partly 2). No cytosolic pool of tetG$_s$α was observed. However, the relative distribution of G$_s$α immunoreactivity in the denser gradient fractions (fractions 3–8) representing cellular membrane components was nearly identical for G$_s$α and tetG$_s$α with the majority of both proteins sedimenting in fraction 6. Thus, it appears that differences in the distribution of G$_s$α and tetG$_s$α in cellular membrane compartments cannot explain the functional differences in receptor-G protein coupling.

Example 10
Generation of Deletion Constructs of tetG$_s$α

Figure 17:
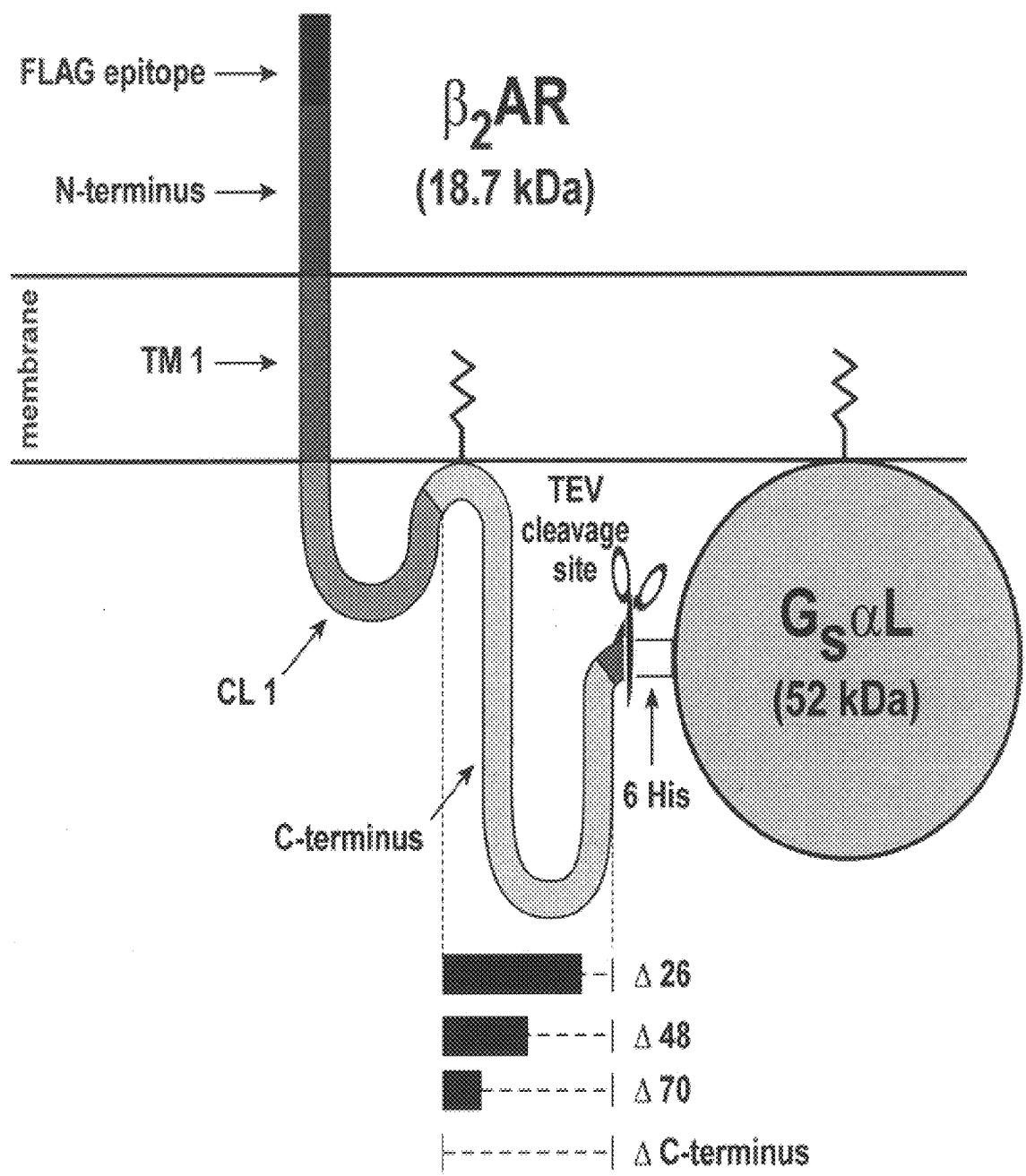
FIG. 17 is a schematic structure of membrane-tethered $G_s\alpha$ deletion mutants.
Figure 18:
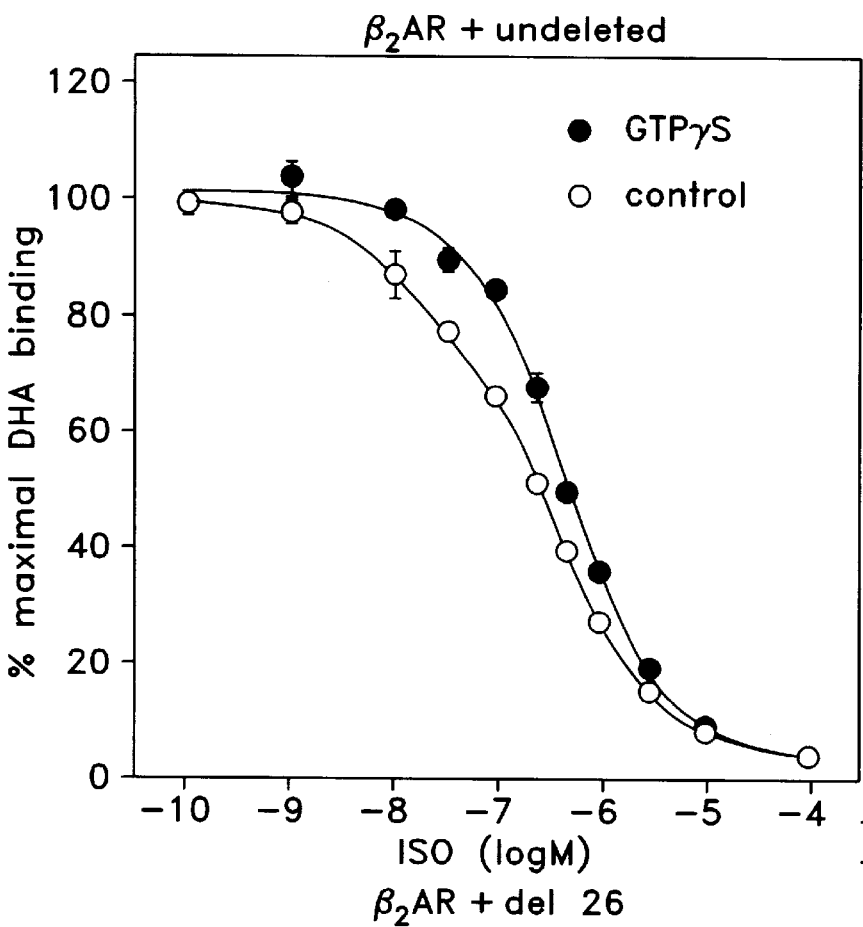
FIGS. 18–22 are graphs illustrating agonist competition binding in Sf9 membranes co-expressing β2 AR and deletion constructs of tetGs.
Figure 19:
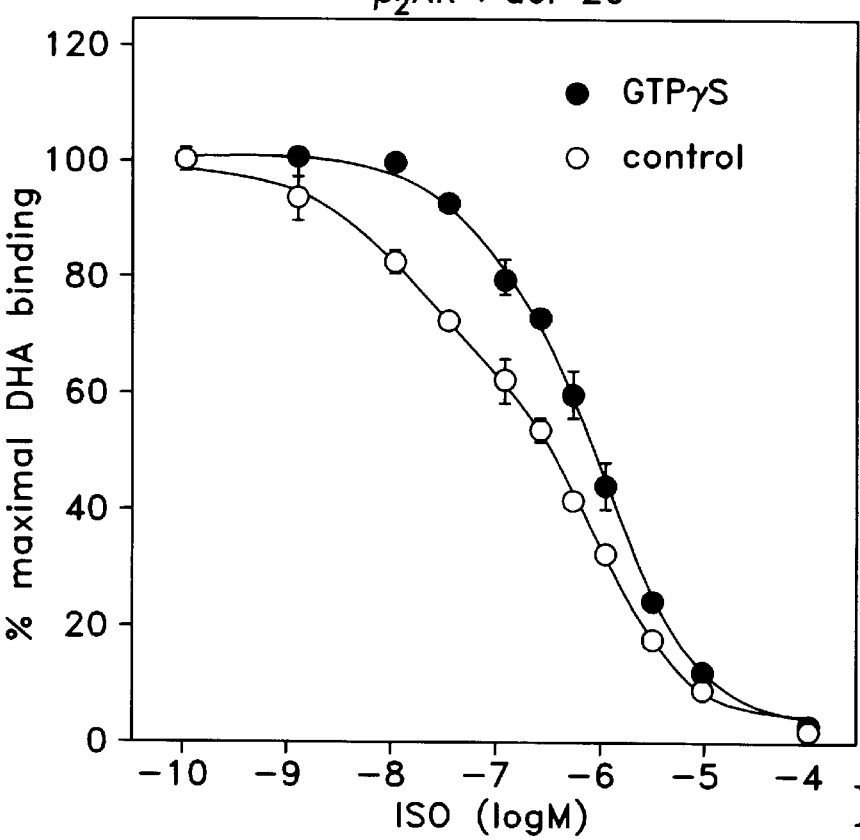
Figure 20:
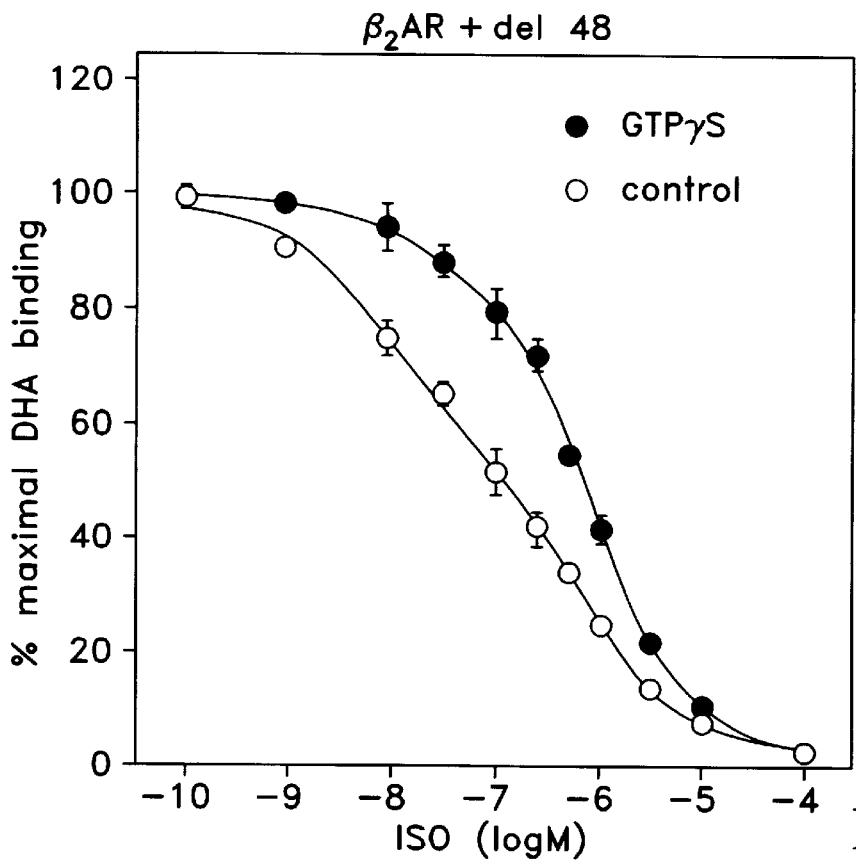
Figure 21:
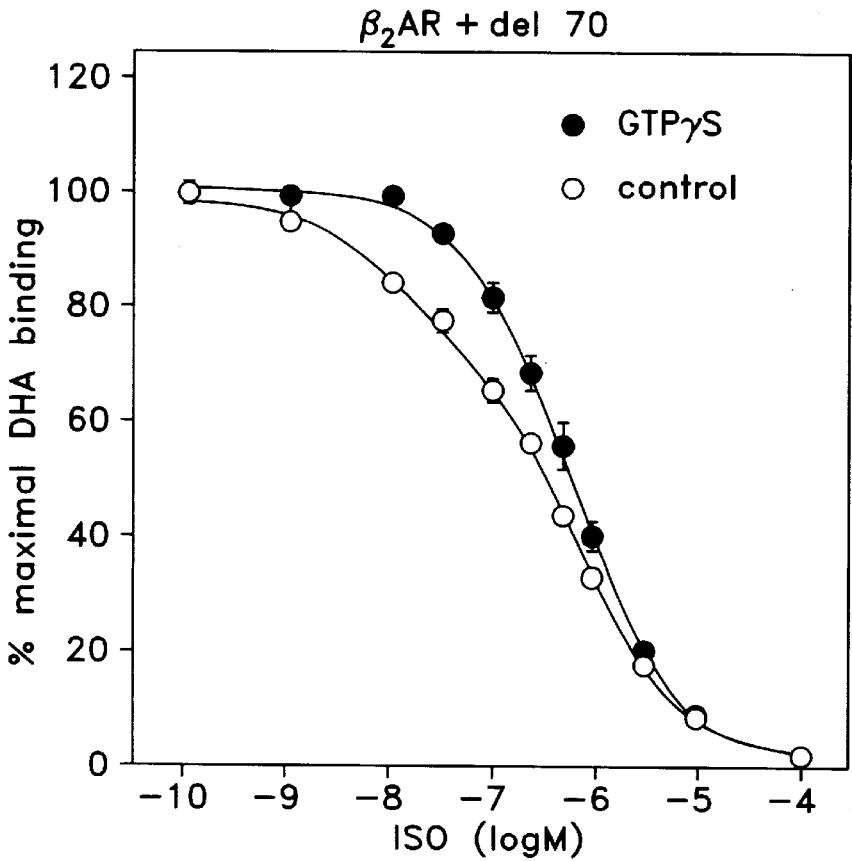
Figure 22:
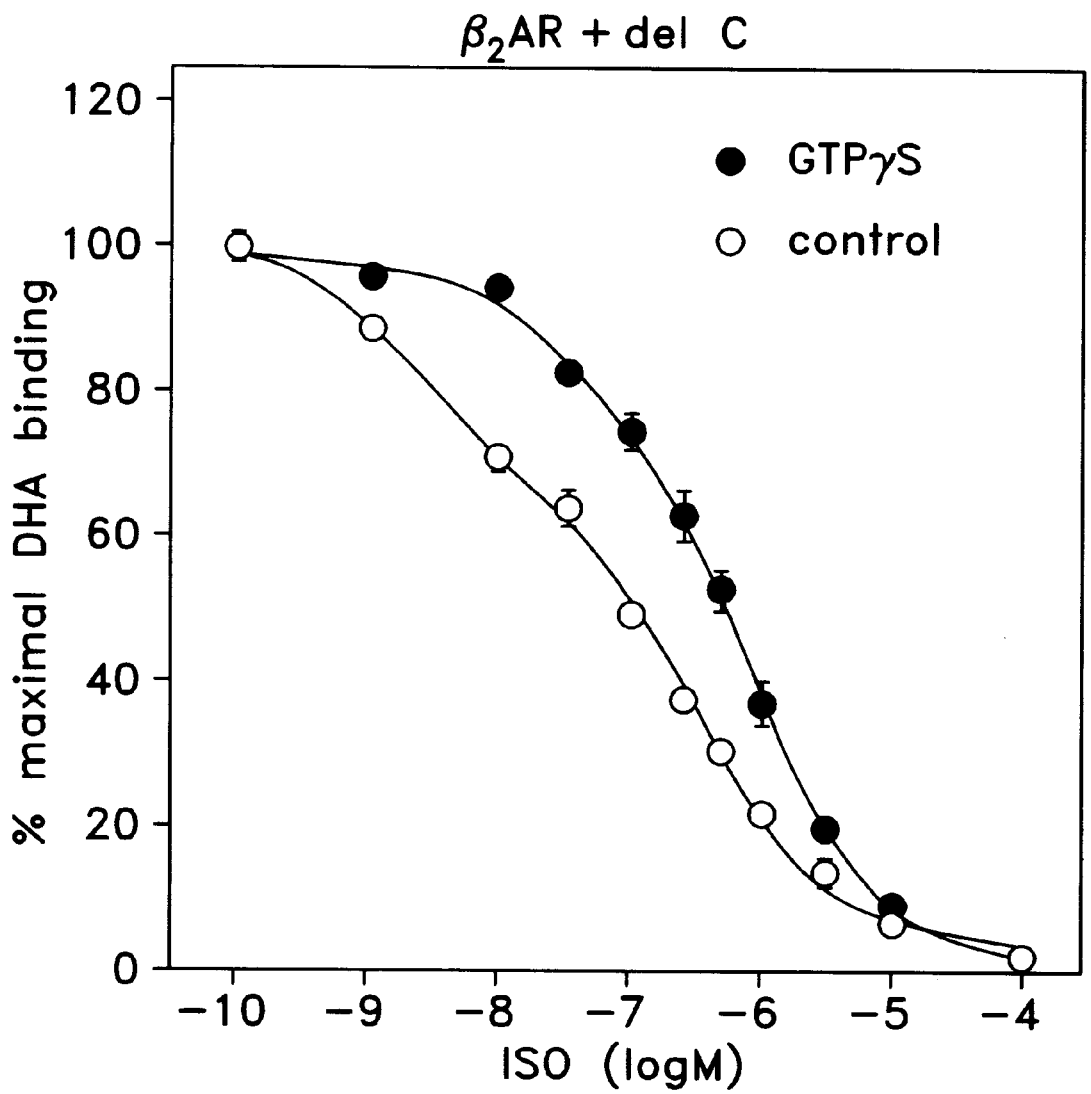
Figure 23:
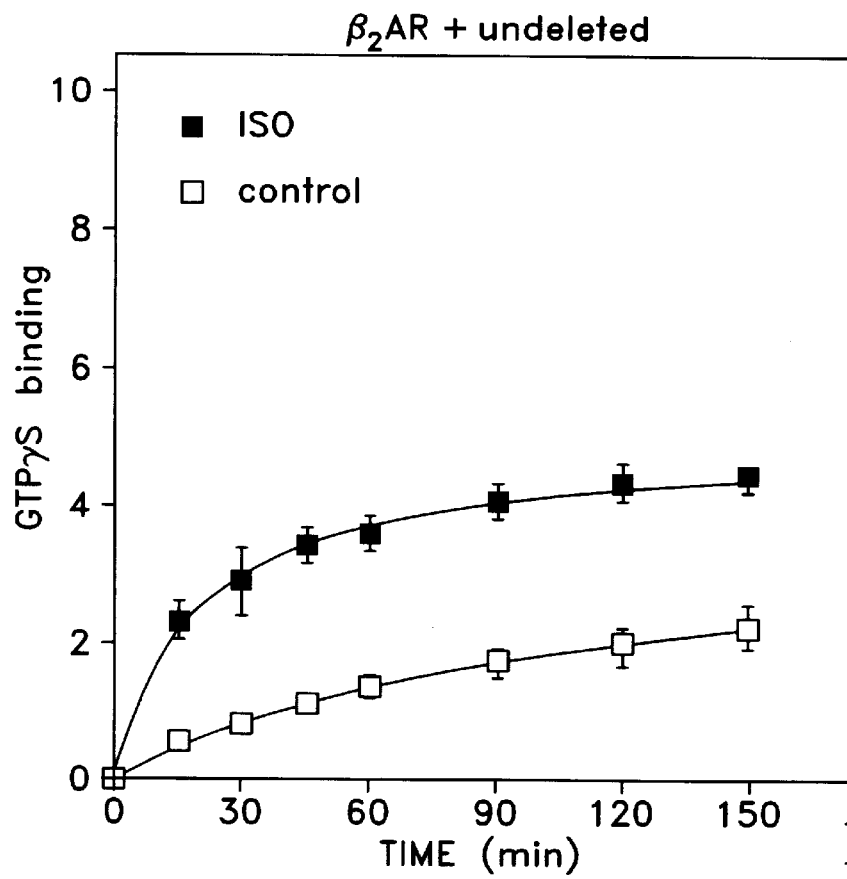
FIGS. 23–27 are graphs illustrating ligand-regulated [$^{35}$S] GTPγS binding in membranes co-expressing β2 AR with deletion constructs of $tetG_s\alpha$.
Figure 24:
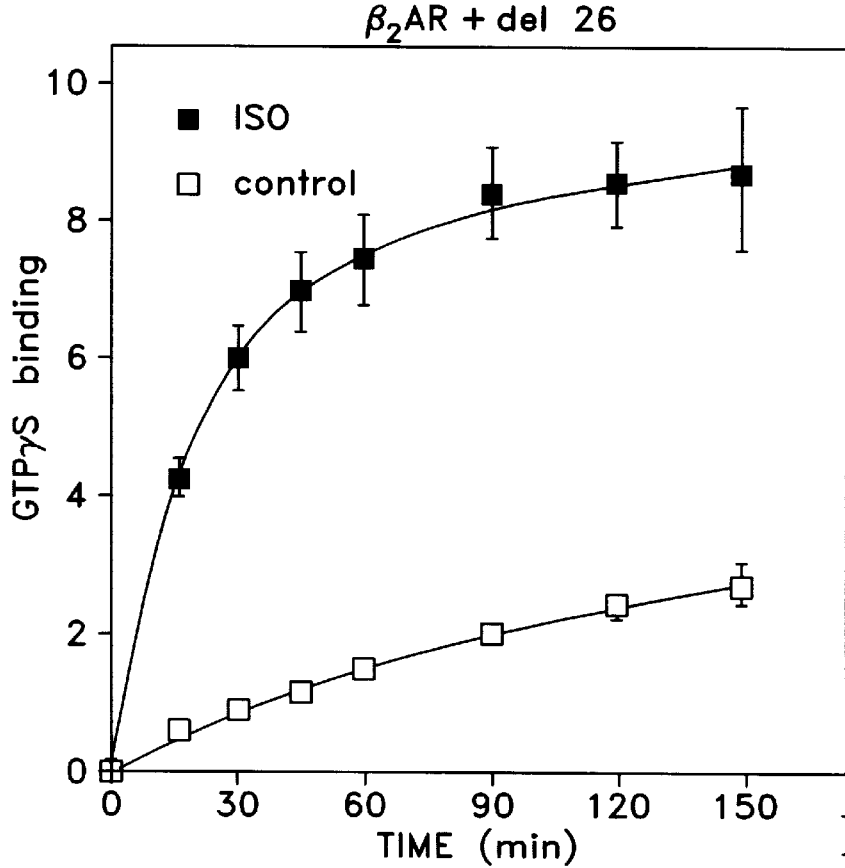
Figure 25:
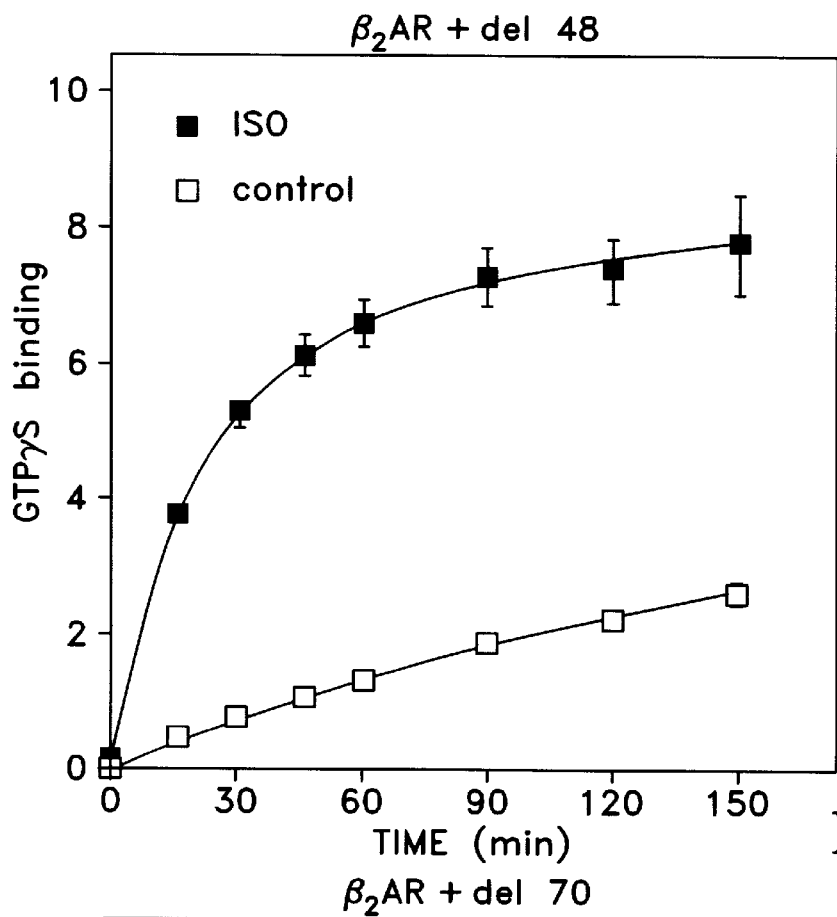
Figure 26:
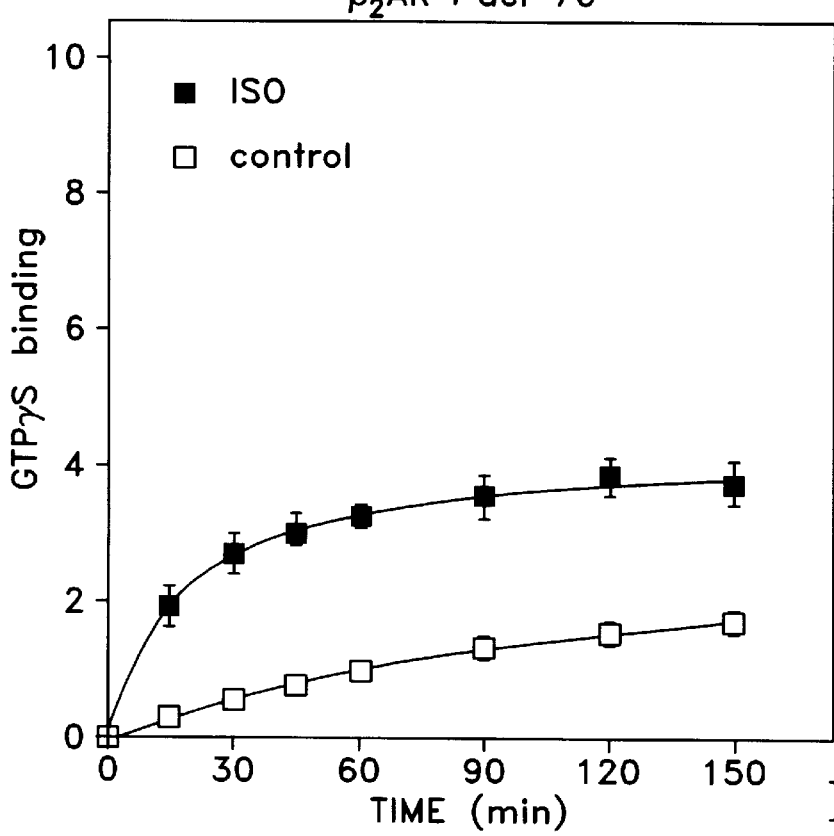
Figure 27:
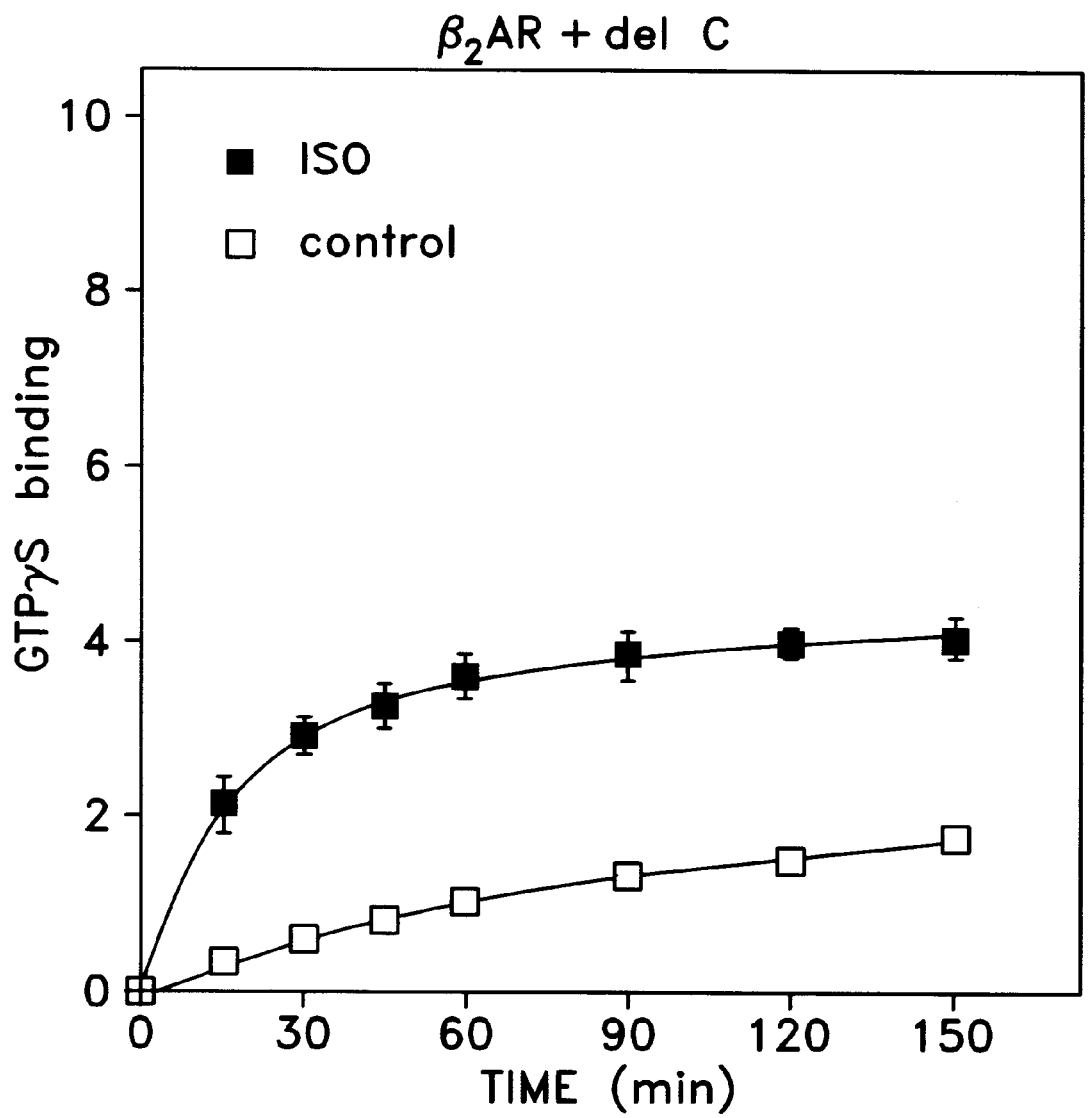
Figure 28:
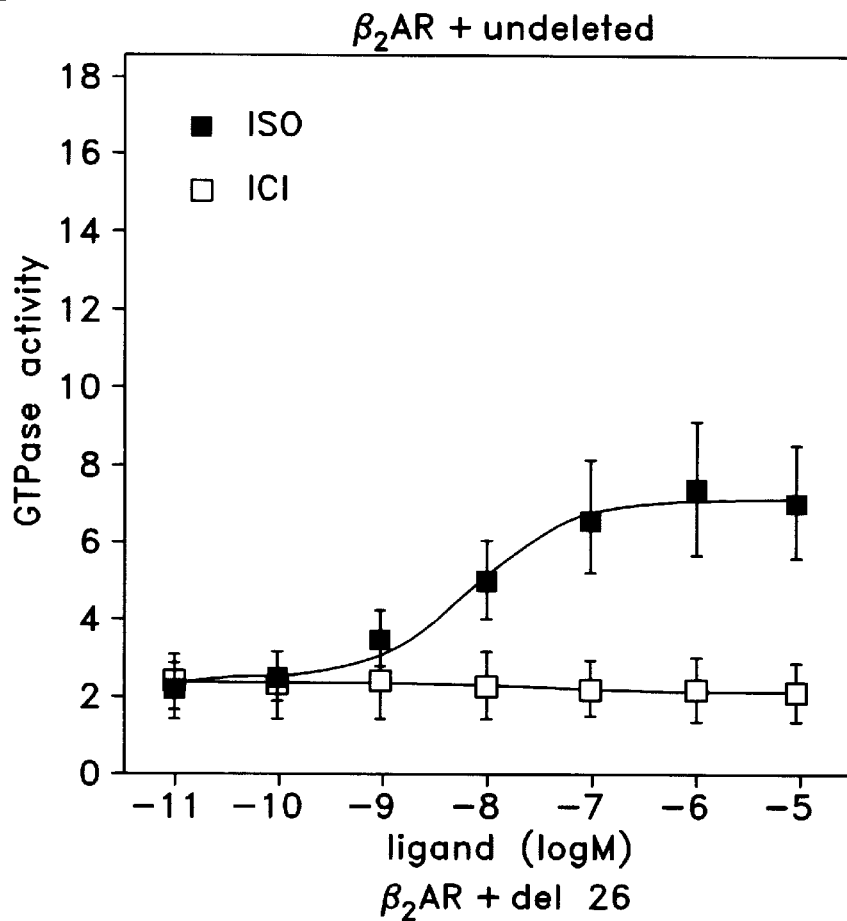
FIGS. 28–32 are graphs illustrating ligand-regulated GTPase activity in membranes co-expressing β2 AR and deletion constructs of $tetG_s\alpha$.
Figure 29:
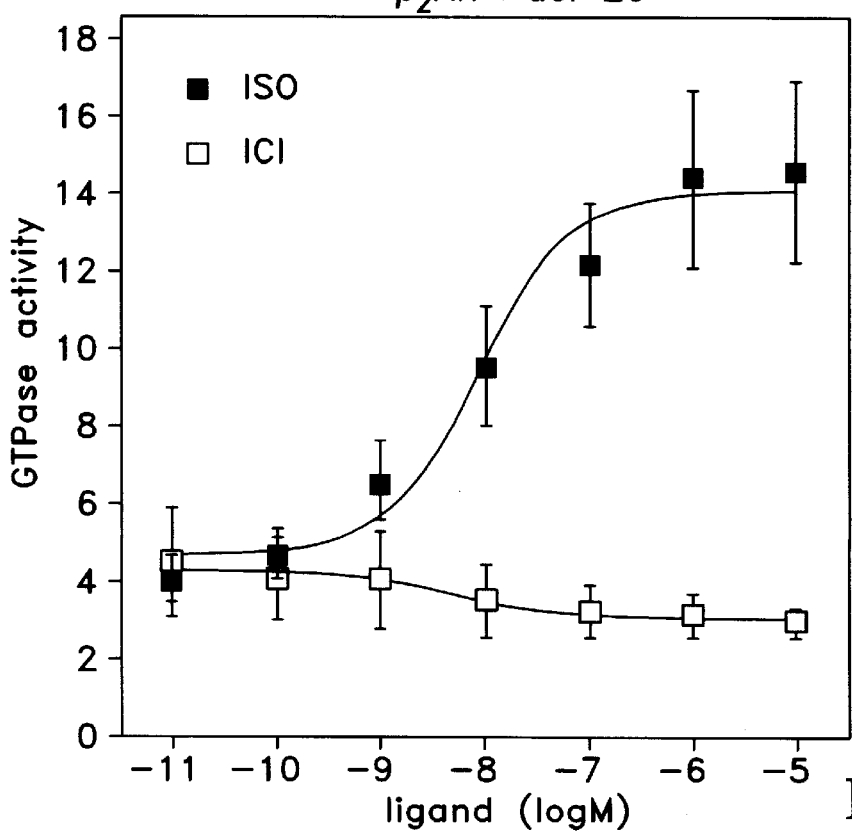
Figure 30:
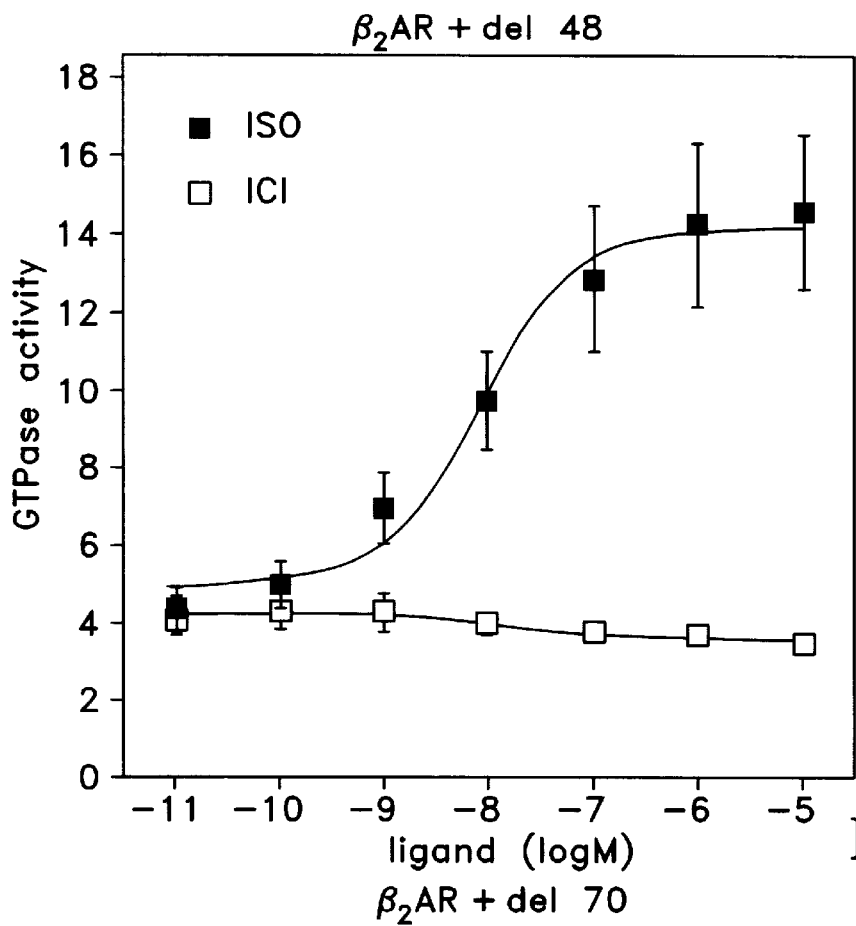
Figure 31:
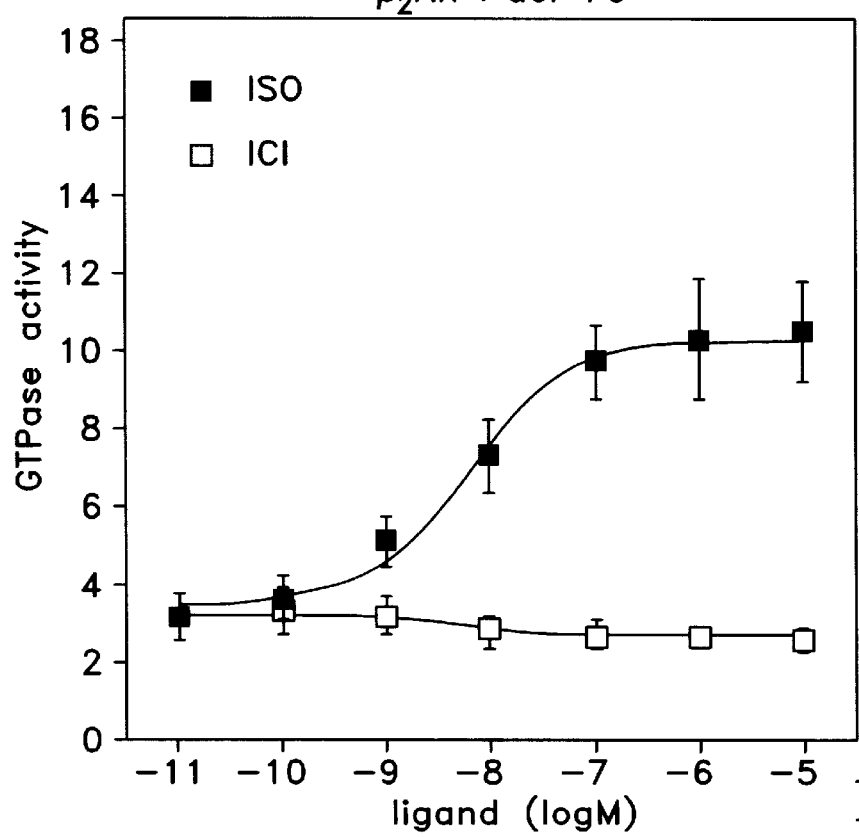
Figure 32:
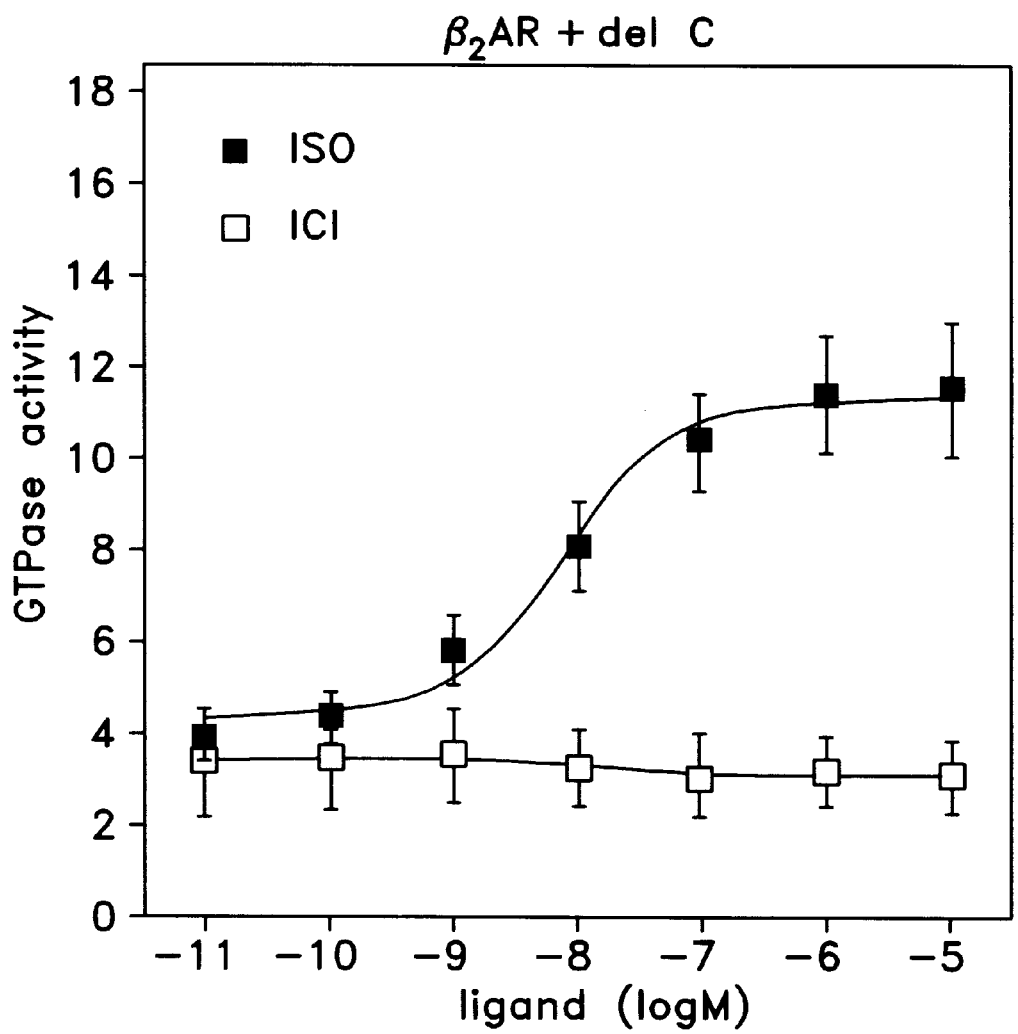
Figure 33:
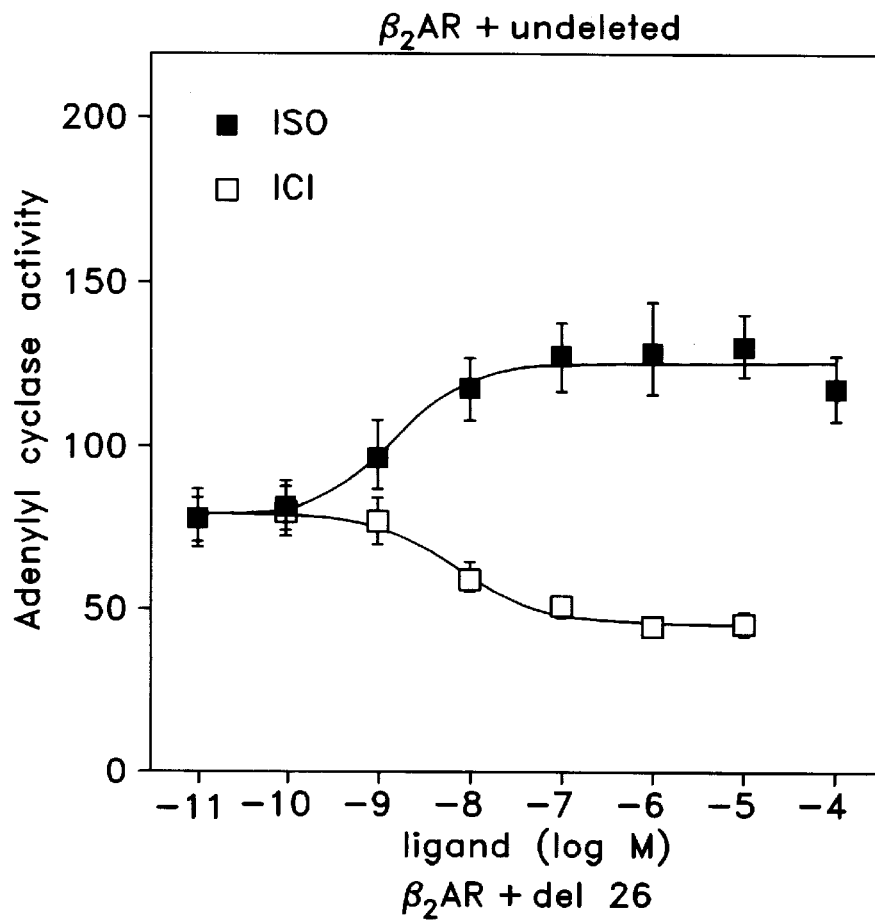
FIGS. 33–37 are graphs illustrating ligand-regulated AC activity in membranes co-expressing β2 AR and deletion constructs of $tetG_s\alpha$.
Figure 34:
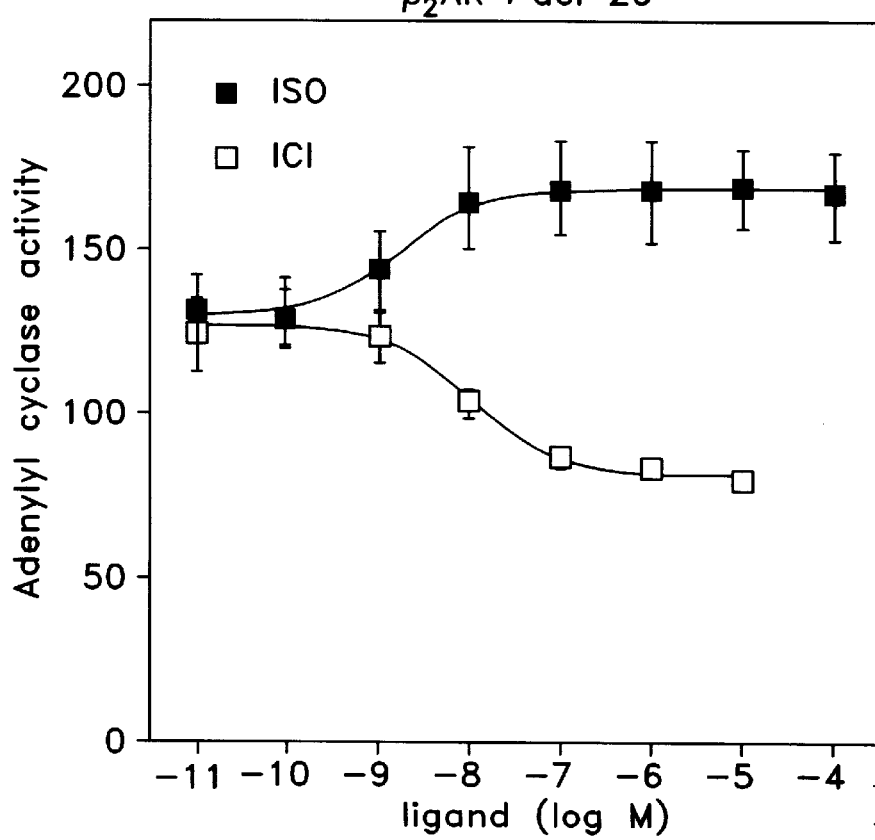
Figure 35:
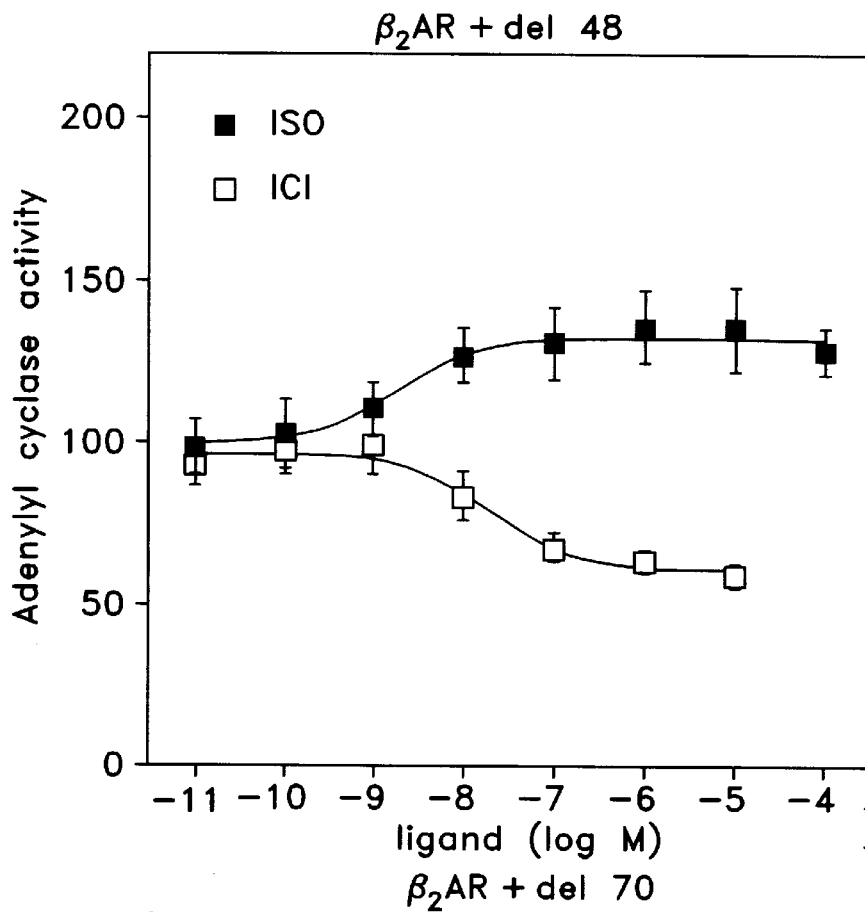
Figure 36:
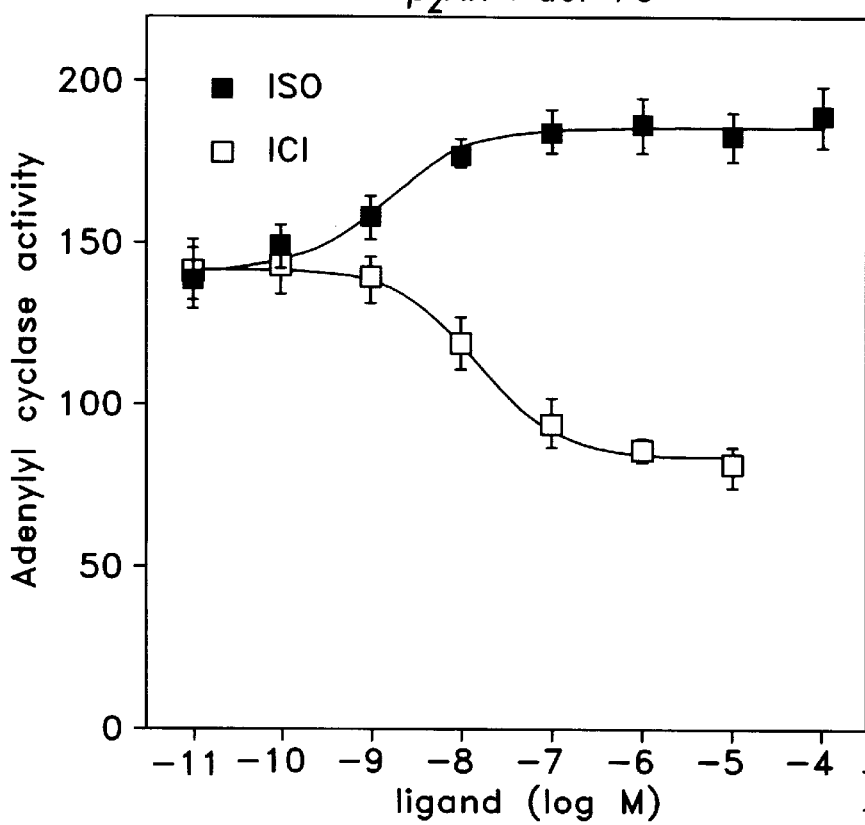
Figure 37:
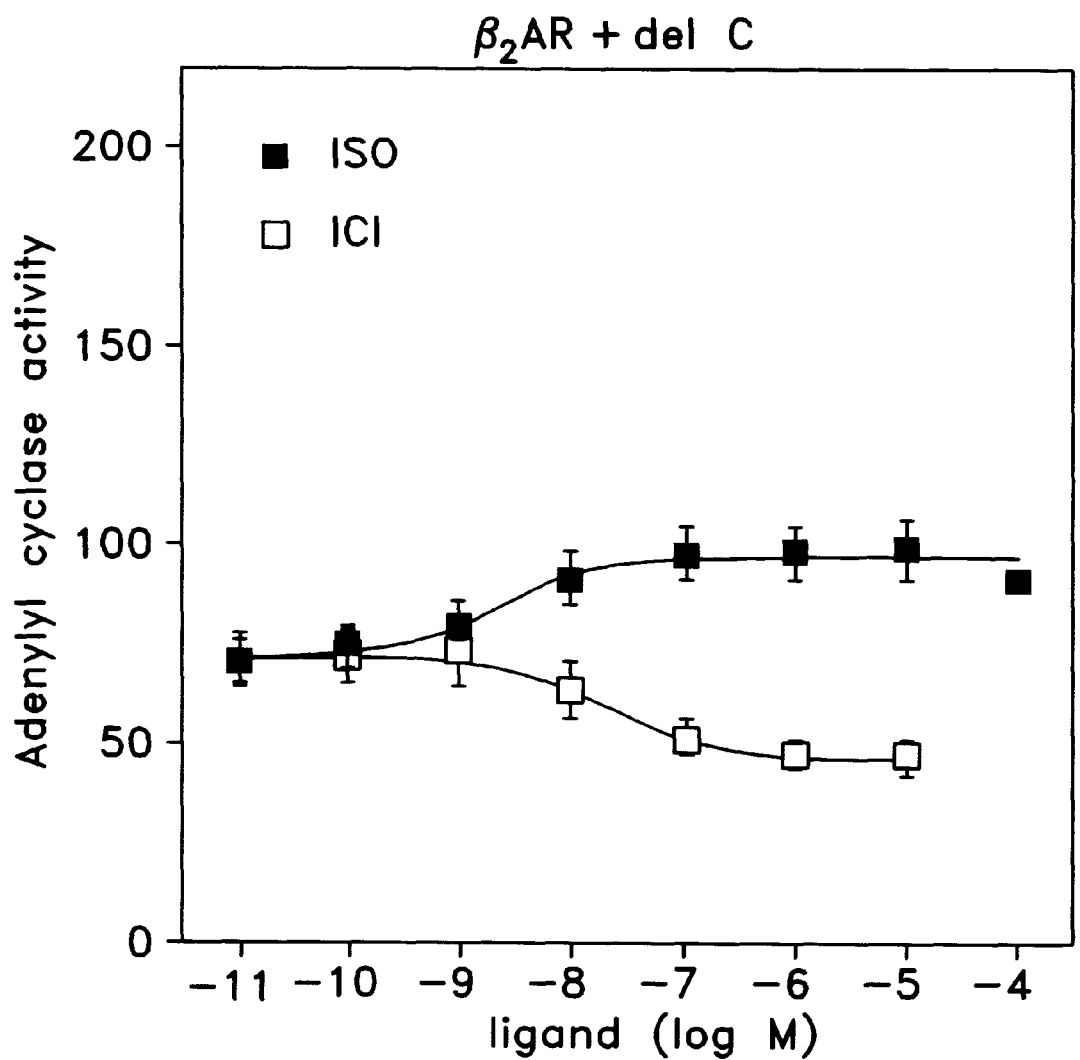

Four deletion constructs, deletion 26(del 26), 48(del 48), 70(del 70) and 84(del C-terminus), were generated by deleting DNA sequences from the C-terminal receptor portion of membrane tetG$_s$α construct (FIG. 17). In these deletion constructs, a SpeI restriction endonuclease site was generated into the baculovirus expression vector pVL1392-(TEV) tetG$_s$α, which has a Spe 1 site on the TEV protease cleavage region encoding site, using overlap extension PCR. For the construction of del 26, for example, first PCR reactions were separately performed with primer sets I+II (sense primer I; 5'-GCCGACTACAAGGACGATGATGAC-3' (SEQ ID NO:6) and antisense primer II; 5'-ACTAGTCTCGAGAAAGTCTTCCGTGCCTGGGAG-3'(SEQ ID NO:7)) and primer sets III+IV (sense primer III; 5'-CTCGAGACTAGTGTGGGCCATCAAGGTACTGTG- 3' (SEQ ID NO:8) and antisense primer IV; 5'-GTCGATCAGCTGGTACTCGTT-3' (SEQ ID NO:9)). For del 48, del 70 and del 84, SpeI site encoding antisense primer II and sense primer III corresponding to each deletion site were used. Overlap extension was performed by primer pairs I and IV. PCR fragments were digested with NcoI and EcoNI to swap with NcoI/EcoNI fragment from pVL1392-(TEV)tetG$_s$α. Constructs containing extra SpeI site in desired deletion sites were digested with SpeI to delete the sequence out and religated. Sequences were confirmed by restriction enzyme digestion and DNA sequencing.

Example 11
Agonist Competition Binding in Membranes Co-expressing β2 AR and Deletion Constructs of tetG$_s$α

Competition binding of [$^3$H]DHA (1 nM) with different concentrations of isoproterenol in membranes co-expressing β82 AR with undeleted (a), del 26 (b), del 48 (c), del 70 (d), and del C (e) in the presence (closed symbol) or absence (open symbol) of 10 μM GTPγS was performed as described in Example 3. Expression levels of β2 AR in each co-expression are 6.7 (undeleted), 7.5 (del 26), 5.4 (del 48), 7.1 (del 70), and 5.2 (del C) pmol/mg, respectively as shown in FIGS. 18–23. Data are expressed as percent of basal bound [$^3$H]DHA, and are the mean±S.E.M. of three independent experiments performed in triplicate.

Example 12
GTPγS Binding in Membranes Coexpressing β2 AR and Deletion Constructs of tetG$_s$α

Ligand-regulated GTPγS binding was determined for membranes co-expressing β2 AR with deletion constructs of tetG$_s$α, as described in Example 5. Membranes (10 μdg) co-expressing β2 AR with undeleted tetG$_s$α (a), del 26 (b), del 48 (c), del 70 (d), and del C tetG$_s$α (e) were incubated with 1 nM [$^{35}$S]GTPγS and 1 μM GDP in the absence (open symbol) or presence (closed symbol) of 10 μM isoproterenol. As shown in FIG. 14, expression levels of β2 AR in each co-expression are 4.3 (undeleted), 7.5 (del 26), 5.4 (del 48), 7.1 (del 70), and 5.2 (del C) pmol/mg, respectively, as shown in FIGS. 23–27. Data shown are mean ±S.E.M. of three independent experiments performed in triplicate.

Example 13
Agonist-Stimulated GTPase Activity of Deletion Constructs of tetG$_s$α from Membranes Coexpressing β2 AR and Deletion Constructs of tetG$_s$α

The basal and agonist-stimulated GTPase activity in Sf9 membranes expressing β2 adrenoceptor and deletion constructs of tetG$_s$α was then examined. GTPase activity was measured as described in Example 4 in the presence of 10 μM isoproterenol (closed symbol) or ICI 118,551 (open symbol) in membranes (10 μg of protein) co-expressing β2 AR with undeleted (a), del 26 (b), del 48 (c), del 70 (d), and del C tetG$_s$α (e) (FIGS. 28–32). Expression levels of β2 AR in each membrane preparation were approximately the same as that shown in Example 4. Data shown are the means±S.E.M. of three independent experiments performed in triplicate.

Example 14
Ligand-regulated AC Activity in Membranes Coexpressing β2 AR and Deletion Constructs of tetG$_s$α

AC activity was measured in Sf9 membranes (20 g of protein) co-expressing β2 AR with undeleted tetG$_s$α (a), del 26 (b), del 48 (c), del 70 (d), and del C (e) in dose response to isoproterenol and ICI 118,551 as described in Example 7 (FIGS. 33–37). Expression levels of β2 AR in each co-expression are approximately the same in each membrane preparation. Data shown are the means ±S.E.M. of three independent experiments performed in triplicate.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for determining the effects of a candidate agent on activation of a G, protein coupled receptor (GPCR), said method comprising;

contacting a candidate agent with a modified G protein a subunit and a GPCR, wherein the modified G protein α subunit and the GPCR are localized to a membrane, and further wherein the modified G protein α subunit comprises a membrane tether and a G protein α subunit, wherein the G protein α subunit is not a fusion protein with the GPCR; and detecting a level of G protein activation in response to said contacting;

wherein the level of G protein activation is inidicative of the effects of tile candidate agent on the activity of the GPCR.

2. The method of claim 1, wherein the modified G protein α subunit is characterized by:

consititutive localization to the membrane;

enhanced binding to a receptor binding partner; and efficient binding to a downstream effector of G protein signaling.

3. The method of claim 1, wherein the modified G protein activation is detected by a level of GTPase activity.

4. The method of claim 1, wherein the modified G protein α subunit is G$_s$α, and further wherein G protein activation is detected by detecting a level of adenylyl cyclase.

5. The method of claim 1, wherein the G protein activation is detected by detecting a level of a fluorescent GTP analog binding to the modified G protein a subunit.

6. The method of claim 1, further comprising:

measuring a level of G protein activation prior to said contacting;

and comparing the level of G protein activation prior to said contacting with the level of G protein activation in response to the candidate agent.

7. The method of claim 1, further comprising comparing the level of G protein activation in response to the candidate agent with a standard indicative of a level of basal G protein activation for the GPCR.

8. The method of claim 4, wherein the GPCR displays spontaneous activity.

9. The method of claim 1, wherein an increase in the level of GPCR activity in response to the compound indicates that the candidate agent is an agonist of the GPCR.

10. The method of claim 1, wherein a decrease in the level G protein activation in response to the candidate agent indicates that the candidate agent as an inverse agonist of the GPCR.

11. The method of claim 1, further comprising:

contacting the modified G protein a subunit and GPCR with an agonist of the CPCR;

wherein a decrease in the level of G protein activation in response to the candidate agent in the presence of the agonist indicates that the candidate agent is an antagonist of the GPCR.

12. The method of claim 1, wherein the membrane is a plasma membrane of whole cells coexpressing the modified G protein α subunit and the GPCR.

13. The method of claim 1, wherein the membrane is provided as a membrane preparation comprising the modified G protein a subunit and the CGPCR.

14. The method of claim 1, wherein the modified G protein α subunit further comprises a heterologous epitope domain.

15. The method of claim 1, wherein the modified G protein α subunit further comprises a protease cleavage site positioned between the tether and the G protein α subunit.

16. A method for determining the effects of a candidate agent on activation of a G protein coupled receptor (GPCR), said method comprising:

contacting a candidate agent with a modified G protein a subunit and a GPCR, wherein the modified G protein α subunit and the GPCR are separate proteins localized to a membrane, and further wherein the modified G protein a subunit comprises, from N-terminus to C-terminus, a membrane tether and a G protein α subunit, wherein the G protein α subunit is not a fusion protein with the GPCR; and detecting a level of G protein activation in response to said contacting;

wherein the level of G protein activation is indicative of the effects of the candidate agent on the activity of the GPCR.

17. The method of claim 16, wherein the membrane tether consists essentially of a transmembrane domain.

18. The method of claim 16, wherein the modified G protein α subunit is characterized by:

consititutive localization to the membrane;

enhanced binding to a receptor binding partner; and efficient binding to a downstream effector of G protein signaling.

19. The method of claim 16, wherein the G protein activation is detected by a level of GTPase activity.

20. The method of claim 16, wherein the modified G protein α subunit is G$_s$α, and further wherein G protein activation is detected by detecting a level of adenylyl cyclase activity.

21. The method of claim 16, wherein the G protein activation is detected by detecting a level of a GTP analog binding to the modified G protein α subunit.

22. The method of claim 16, further comprising:

measuring a level of G protein activation prior to said contacting;

and comparing the level of G protein activation prior to said contacting with the level of G protein activation in response to the candidate agent.

23. The method of claim 16, further comprising comparing the level of G protein activation in response to the candidate agent with a standard indicative of a level of basal G protein activation for the GPCR.

24. The method of claim 20, wherein the GPCR displays spontaneous activity.

25. The method of claim 16, wherein an increase in the level of GPCR activity in response to the compound indicates that the candidate agent is an agonist of the GPCR.

26. The method of claim 16, wherein a decrease in the level G protein activation in response to the candidate agent indicates that the candidate agent as an inverse agonist of the GPCR.

27. The method of claim 16, further comprising:

contacting the modified G protein a subunit and GPCR with an agonist of the GPCR;

wherein a decrease in the level of G protein activation in response to the candidate agent in the presence of the agonist indicates that the candidate agent is an antagonist of the GPCR.

28. The method of claim 16, wherein the membrane is a plasma membrane of whole cells coexpressing the modified G protein α subunit aid the GPCR.

29. The method of claim 16, wherein the membrane is provided as a membrane preparation comprising the modified G protein α subunit and the GPCR.

30. The method of claim 16, wherein the modified G protein α subunit further comprises a heterologous epitope domain.

31. The method of claim 16, wherein the modified G protein α subunit further comprises a protease cleavage site positioned between the tether and the G protein α subunit.

* * * * *